(12) United States Patent
Wang et al.

(10) Patent No.: US 8,066,858 B2
(45) Date of Patent: Nov. 29, 2011

(54) ANALYTE SENSOR WITH INSERTION MONITOR, AND METHODS

(75) Inventors: Yi Wang, San Ramon, CA (US); Joseph A. Vivolo, San Francisco, CA (US); Shridhara Alva Karinka, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 433 days.

(21) Appl. No.: 11/932,658

(22) Filed: Oct. 31, 2007

(65) Prior Publication Data

US 2008/0283396 A1 Nov. 20, 2008

Related U.S. Application Data

(63) Continuation of application No. 11/281,883, filed on Nov. 17, 2005, which is a continuation-in-part of application No. 10/866,477, filed on Jun. 12, 2004, now abandoned, which is a continuation of application No. 10/033,575, filed on Dec. 28, 2001, now Pat. No. 6,749,740, which is a continuation of application No. 09/434,026, filed on Nov. 4, 1999, now Pat. No. 6,616,819.

(51) Int. Cl.
*G01N 27/416* (2006.01)
*G01N 27/327* (2006.01)

(52) U.S. Cl. .................................. 204/406; 204/403.02

(58) Field of Classification Search ............. 204/403.01, 204/403.02, 403.04, 406
See application file for complete search history.

(56) References Cited

U.S. PATENT DOCUMENTS

| | | | |
|---|---|---|---|
| 3,260,656 A | 7/1966 | Ross, Jr. | |
| 3,653,841 A | 4/1972 | Klein | |
| 3,719,564 A | 3/1973 | Lilly, Jr. et al. | |
| 3,776,832 A | 12/1973 | Oswin et al. | |
| 3,837,339 A | 9/1974 | Aisenberg et al. | |
| 3,972,320 A | 8/1976 | Kalman | |
| 3,979,274 A | 9/1976 | Newman | |
| 4,008,717 A | 2/1977 | Kowarski | |
| 4,016,866 A | 4/1977 | Lawton | |
| 4,055,175 A | 10/1977 | Clemens et al. | |
| 4,059,406 A | 11/1977 | Fleet | |
| 4,076,596 A | 2/1978 | Connery et al. | |

(Continued)

FOREIGN PATENT DOCUMENTS

DE 2903216 8/1979

(Continued)

OTHER PUBLICATIONS

Abruna, H. D. et al., "Rectifying Interfaces Using Two-Layer Films of Electrochemically Polymerized Vinylpyridine and Vinylpyridine Complexes of Ruthenium and Iron on Electrodes," J. Am. Chem. Soc., 103(1):1-5 (Jan. 14, 1981).

(Continued)

*Primary Examiner* — Kaj K Olsen
(74) *Attorney, Agent, or Firm* — Edward J. Baba; Marcus Hunt; Bozicevic, Field & Francis LLP

(57) ABSTRACT

A sensor, and methods of making, for determining the concentration of an analyte, such as glucose or lactate, in a biological fluid such as blood or serum, using techniques such as coulometry, amperometry, and potentiometry. The sensor includes a working electrode and a counter electrode, and can include an insertion monitoring trace to determine correct positioning of the sensor in a connector.

11 Claims, 10 Drawing Sheets

U.S. PATENT DOCUMENTS

| | | |
|---|---|---|
| 4,098,574 A | 7/1978 | Dappen |
| 4,100,048 A | 7/1978 | Pompei et al. |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,247,297 A | 1/1981 | Berti et al. |
| 4,271,119 A | 6/1981 | Columbus |
| 4,318,784 A | 3/1982 | Higgins et al. |
| 4,340,458 A | 7/1982 | Lerner et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,418,148 A | 11/1983 | Oberhardt |
| 4,420,564 A | 12/1983 | Tsuji et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,444,892 A | 4/1984 | Malmros |
| 4,450,842 A | 5/1984 | Zick et al. |
| 4,461,691 A | 7/1984 | Frank |
| 4,469,110 A | 9/1984 | Slama |
| 4,477,314 A | 10/1984 | Richter et al. |
| 4,483,924 A | 11/1984 | Tsuji et al. |
| 4,484,987 A | 11/1984 | Gough |
| 4,522,690 A | 6/1985 | Venkatasetty |
| 4,524,114 A | 6/1985 | Samuels et al. |
| 4,526,661 A | 7/1985 | Steckhan et al. |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,580,564 A | 4/1986 | Andersen |
| 4,581,336 A | 4/1986 | Malloy et al. |
| 4,595,011 A | 6/1986 | Phillips |
| 4,595,479 A | 6/1986 | Kimura et al. |
| 4,619,754 A | 10/1986 | Niki et al. |
| 4,633,878 A | 1/1987 | Bombardieri |
| 4,637,403 A | 1/1987 | Garcia et al. |
| 4,650,547 A | 3/1987 | Gough |
| 4,654,127 A | 3/1987 | Baker et al. |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,703,756 A | 11/1987 | Gough et al. |
| 4,711,245 A | 12/1987 | Higgins et al. |
| 4,714,874 A | 12/1987 | Morris et al. |
| 4,717,673 A | 1/1988 | Wrighton et al. |
| 4,721,601 A | 1/1988 | Wrighton et al. |
| 4,726,378 A | 2/1988 | Kaplan |
| 4,750,496 A | 6/1988 | Reinhart et al. |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,781,798 A | 11/1988 | Gough |
| 4,784,736 A | 11/1988 | Lonsdale et al. |
| 4,795,707 A | 1/1989 | Niiyama et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,840,893 A | 6/1989 | Hill et al. |
| 4,848,351 A | 7/1989 | Finch |
| 4,854,153 A | 8/1989 | Miyagawa et al. |
| 4,871,351 A | 10/1989 | Feingold |
| 4,871,440 A | 10/1989 | Nagata et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,919,141 A | 4/1990 | Zier et al. |
| 4,919,767 A | 4/1990 | Vadgama et al. |
| 4,923,586 A | 5/1990 | Katayama et al. |
| 4,927,516 A | 5/1990 | Yamaguchi et al. |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,945,045 A | 7/1990 | Forrest et al. |
| 4,950,378 A | 8/1990 | Nagata |
| 4,953,552 A | 9/1990 | DeMarzo |
| 4,954,087 A | 9/1990 | Lauks et al. |
| 4,968,400 A | 11/1990 | Shimomura et al. |
| 4,970,145 A | 11/1990 | Bennetto et al. |
| 4,974,929 A | 12/1990 | Curry |
| 4,986,271 A | 1/1991 | Wilkins |
| 4,994,167 A | 2/1991 | Shults et al. |
| 4,999,582 A | 3/1991 | Parks et al. |
| 5,026,388 A | 6/1991 | Ingalz |
| 5,034,192 A | 7/1991 | Wrighton et al. |
| 5,037,527 A | 8/1991 | Hayashi et al. |
| 5,053,199 A | 10/1991 | Keiser et al. |
| 5,070,535 A | 12/1991 | Hochmair et al. |
| 5,078,854 A | 1/1992 | Burgess et al. |
| 5,082,550 A | 1/1992 | Rishpon et al. |
| 5,082,786 A | 1/1992 | Nakamoto |
| 5,089,112 A | 2/1992 | Skotheim et al. |
| 5,094,951 A | 3/1992 | Rosenberg |
| 5,096,560 A | 3/1992 | Takai et al. |
| 5,096,836 A | 3/1992 | Macho et al. |
| 5,101,814 A | 4/1992 | Palti |
| 5,108,564 A | 4/1992 | Szuminsky et al. |
| 5,109,850 A | 5/1992 | Blanco et al. |
| 5,120,420 A | 6/1992 | Nankai et al. |
| 5,120,421 A | 6/1992 | Glass et al. |
| 5,126,034 A | 6/1992 | Carter et al. |
| 5,126,247 A | 6/1992 | Palmer et al. |
| 5,128,015 A | 7/1992 | Szuminsky et al. |
| 5,130,009 A | 7/1992 | Marsoner et al. |
| 5,133,856 A | 7/1992 | Yamaguchi et al. |
| 5,140,393 A | 8/1992 | Hijikihigawa et al. |
| 5,141,868 A | 8/1992 | Shanks et al. |
| 5,160,278 A | 11/1992 | Johnson |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,185,256 A | 2/1993 | Nankai et al. |
| 5,192,415 A | 3/1993 | Yoshioka et al. |
| 5,192,416 A | 3/1993 | Wang et al. |
| 5,198,367 A | 3/1993 | Aizawa et al. |
| 5,200,051 A | 4/1993 | Cozzette et al. |
| 5,201,324 A | 4/1993 | Swierczek |
| 5,202,261 A | 4/1993 | Musho et al. |
| 5,205,920 A | 4/1993 | Oyama et al. |
| 5,206,145 A | 4/1993 | Cattell |

| Patent No. | Date | Inventor |
|---|---|---|
| 5,208,154 A | 5/1993 | Weaver et al. |
| 5,217,595 A | 6/1993 | Smith et al. |
| 5,227,042 A | 7/1993 | Zawodzinski et al. |
| 5,229,282 A | 7/1993 | Yoshioka et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,106 A | 11/1993 | McAleer et al. |
| 5,266,179 A | 11/1993 | Nankai et al. |
| 5,271,815 A | 12/1993 | Wong |
| 5,272,060 A | 12/1993 | Hamamoto et al. |
| 5,278,079 A | 1/1994 | Gubinski et al. |
| 5,282,950 A | 2/1994 | Dietze et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,310,885 A | 5/1994 | Maier et al. |
| 5,320,725 A | 6/1994 | Gregg et al. |
| 5,320,732 A | 6/1994 | Nankai et al. |
| 5,326,449 A | 7/1994 | Cunningham |
| 5,337,747 A | 8/1994 | Neftel |
| 5,352,348 A | 10/1994 | Young et al. |
| 5,352,351 A | 10/1994 | White et al. |
| 5,356,786 A | 10/1994 | Heller et al. |
| 5,364,797 A | 11/1994 | Olson et al. |
| 5,366,609 A * | 11/1994 | White et al. ............. 204/403.04 |
| 5,368,028 A | 11/1994 | Palti |
| 5,372,133 A | 12/1994 | Hogen Esch |
| 5,378,628 A | 1/1995 | Gratzel et al. |
| 5,380,422 A | 1/1995 | Negishi et al. |
| 5,382,346 A | 1/1995 | Uenoyama et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,410,474 A | 4/1995 | Fox |
| 5,411,647 A | 5/1995 | Johnson et al. |
| 5,413,690 A | 5/1995 | Kost et al. |
| 5,422,246 A | 6/1995 | Koopal et al. |
| 5,435,735 A * | 7/1995 | Wittig et al. .................... 439/79 |
| 5,437,973 A | 8/1995 | Vadgama et al. |
| 5,437,999 A | 8/1995 | Diebold et al. |
| 5,438,271 A | 8/1995 | White et al. |
| 5,478,751 A | 12/1995 | Oosta et al. |
| 5,494,562 A | 2/1996 | Maley et al. |
| 5,496,453 A | 3/1996 | Uenoyama et al. |
| 5,497,772 A | 3/1996 | Schulman et al. |
| 5,501,956 A | 3/1996 | Wada et al. |
| 5,502,396 A | 3/1996 | Desarzens et al. |
| 5,507,288 A | 4/1996 | Bocker et al. |
| 5,508,171 A | 4/1996 | Walling et al. |
| 5,514,253 A | 5/1996 | Davis et al. |
| 5,520,787 A | 5/1996 | Hanagan et al. |
| 5,525,511 A | 6/1996 | D'Costa |
| 5,526,120 A | 6/1996 | Jina et al. |
| 5,531,878 A | 7/1996 | Vadgama et al. |
| 5,552,027 A | 9/1996 | Birkle et al. |
| 5,556,524 A | 9/1996 | Albers |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,132 A | 11/1996 | Mawhirt et al. |
| 5,575,895 A | 11/1996 | Ikeda et al. |
| 5,580,527 A | 12/1996 | Bell et al. |
| 5,582,184 A | 12/1996 | Erickson et al. |
| 5,582,697 A | 12/1996 | Ikeda et al. |
| 5,582,698 A | 12/1996 | Flaherty et al. |
| 5,586,553 A | 12/1996 | Halili et al. |
| 5,589,045 A | 12/1996 | Hyodo |
| 5,589,326 A | 12/1996 | Deng et al. |
| 5,593,852 A | 1/1997 | Heller et al. |
| 5,596,150 A | 1/1997 | Arndt et al. |
| 5,599,479 A | 2/1997 | Kimura et al. |
| 5,617,851 A | 4/1997 | Lipkovker |
| 5,628,890 A | 5/1997 | Carter et al. |
| 5,650,062 A | 7/1997 | Ikeda et al. |
| 5,651,869 A | 7/1997 | Yoshioka et al. |
| 5,660,163 A | 8/1997 | Schulman et al. |
| 5,665,215 A | 9/1997 | Bussmann et al. |
| 5,670,031 A | 9/1997 | Hintsche et al. |
| 5,680,858 A | 10/1997 | Hansen et al. |
| 5,680,872 A | 10/1997 | Sesekura et al. |
| 5,682,233 A | 10/1997 | Brinda |
| 5,694,932 A | 12/1997 | Michel |
| 5,695,623 A | 12/1997 | Michel et al. |
| 5,708,247 A | 1/1998 | McAleer et al. |
| 5,711,861 A | 1/1998 | Ward et al. |
| 5,711,862 A | 1/1998 | Sakoda et al. |
| 5,720,862 A | 2/1998 | Hamamoto et al. |
| 5,727,548 A | 3/1998 | Hill et al. |
| 5,730,753 A | 3/1998 | Morita |
| 5,741,211 A | 4/1998 | Renirie et al. |
| 5,741,688 A | 4/1998 | Oxenboll et al. |
| 5,746,217 A | 5/1998 | Erickson et al. |
| 5,759,364 A | 6/1998 | Charlton et al. |
| 5,770,028 A | 6/1998 | Maley et al. |
| 5,780,304 A | 7/1998 | Matzinger et al. |
| 5,781,455 A | 7/1998 | Hyodo |
| 5,791,344 A | 8/1998 | Schulman et al. |
| 5,801,057 A | 9/1998 | Smart et al. |
| 5,804,048 A | 9/1998 | Wong et al. |
| 5,820,570 A | 10/1998 | Erickson et al. |
| 5,830,341 A | 11/1998 | Gilmartin |
| 5,834,224 A | 11/1998 | Ruger et al. |
| 5,837,454 A | 11/1998 | Cozzette et al. |
| 5,837,546 A | 11/1998 | Allen et al. |
| 5,839,916 A | 11/1998 | Chishima |
| 5,842,883 A | 12/1998 | Igarashi et al. |
| 5,842,983 A | 12/1998 | Abel et al. |
| 5,846,702 A | 12/1998 | Deng et al. |
| 5,846,744 A | 12/1998 | Athey et al. |
| 5,856,195 A | 1/1999 | Charlton et al. |
| 5,857,983 A | 1/1999 | Douglas et al. |
| 5,873,990 A | 2/1999 | Wojciechowski et al. |
| 5,879,311 A | 3/1999 | Duchon et al. |
| 5,902,253 A | 5/1999 | Pfeiffer et al. |
| 5,934,933 A | 8/1999 | Kordecki et al. |
| 5,951,836 A | 9/1999 | McAleer et al. |
| 5,964,718 A | 10/1999 | Duchon et al. |
| 5,968,836 A | 10/1999 | Matzinger et al. |
| 5,971,941 A | 10/1999 | Simons et al. |
| 5,997,817 A | 12/1999 | Crismore et al. |
| 6,004,441 A | 12/1999 | Fujiwara et al. |
| 6,015,392 A | 1/2000 | Douglas et al. |
| 6,033,866 A | 3/2000 | Guo et al. |
| 6,053,930 A | 4/2000 | Ruppert |
| 6,071,391 A | 6/2000 | Gotoh et al. |
| 6,120,676 A | 9/2000 | Heller et al. |
| 6,143,164 A | 11/2000 | Heller et al. |
| 6,153,069 A | 11/2000 | Pottgen et al. |
| 6,156,173 A | 12/2000 | Gotoh et al. |
| 6,162,397 A | 12/2000 | Jurik et al. |
| 6,168,957 B1 | 1/2001 | Matzinger et al. |
| 6,200,442 B1 | 3/2001 | Markart |
| 6,207,000 B1 | 3/2001 | Schwobel et al. |
| 6,258,229 B1 | 7/2001 | Winarta et al. |
| 6,283,982 B1 | 9/2001 | Levaughn et al. |
| 6,287,451 B1 | 9/2001 | Winarta et al. |
| 6,299,757 B1 | 10/2001 | Feldman et al. |
| 6,332,871 B1 | 12/2001 | Douglas et al. |
| 6,356,774 B1 | 3/2002 | Bernstein et al. |
| 6,377,894 B1 | 4/2002 | Deweese et al. |
| 6,461,496 B1 | 10/2002 | Feldman et al. |
| 6,464,649 B1 | 10/2002 | Duchon et al. |
| 6,503,381 B1 | 1/2003 | Gotoh et al. |
| 6,558,402 B1 | 5/2003 | Chelak et al. |
| 6,562,625 B2 | 5/2003 | Modzelewski et al. |
| 6,599,406 B1 | 7/2003 | Kawanaka et al. |
| 6,616,819 B1 | 9/2003 | Liamos et al. |
| 6,743,635 B2 | 6/2004 | Neel et al. |
| 6,749,740 B2 | 6/2004 | Liamos et al. |
| 6,766,817 B2 | 7/2004 | da Silva |
| 6,780,645 B2 | 8/2004 | Hayter et al. |

| | | | |
|---|---|---|---|
| 6,814,844 B2 | 11/2004 | Bhullar et al. | |
| 6,827,829 B2 * | 12/2004 | Kawanaka et al. | 204/403.02 |
| 6,866,758 B2 | 3/2005 | Bhullar et al. | |
| 6,875,327 B1 | 4/2005 | Miyazaki et al. | |
| 7,340,309 B2 | 3/2008 | Miazga et al. | |
| D583,691 S | 12/2008 | Wang | |
| D587,142 S | 2/2009 | Wang | |
| 2003/0159945 A1 | 8/2003 | Miyazaki et al. | |
| 2004/0094432 A1 * | 5/2004 | Neel et al. | 205/777.5 |
| 2004/0178066 A1 | 9/2004 | Miyazaki et al. | |
| 2004/0178067 A1 | 9/2004 | Miyazaki et al. | |
| 2004/0225230 A1 | 11/2004 | Liamos et al. | |
| 2004/0244151 A1 | 12/2004 | Sakata et al. | |
| 2005/0016845 A1 | 1/2005 | Groll et al. | |
| 2006/0091006 A1 | 5/2006 | Wang et al. | |
| 2006/0191787 A1 | 8/2006 | Wang et al. | |
| 2008/0105024 A1 | 5/2008 | Creaven et al. | |
| 2009/0029479 A1 | 1/2009 | Docherty et al. | |

FOREIGN PATENT DOCUMENTS

| | | |
|---|---|---|
| DE | 227029 | 9/1985 |
| EP | 0048090 | 3/1982 |
| EP | 0078636 | 5/1983 |
| EP | 0080304 | 6/1983 |
| EP | 0096288 | 12/1983 |
| EP | 0136362 | 4/1984 |
| EP | 0125139 | 11/1984 |
| EP | 0127958 | 12/1984 |
| EP | 0170375 | 2/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0286084 | 10/1988 |
| EP | 0359831 | 3/1990 |
| EP | 0368209 | 5/1990 |
| EP | 0390390 | 10/1990 |
| EP | 0400918 | 12/1990 |
| EP | 0453283 | 10/1991 |
| EP | 0470290 | 2/1992 |
| EP | 0537761 | 4/1993 |
| EP | 0781406 | 7/1997 |
| GB | 1394171 | 5/1975 |
| GB | 2073891 | 10/1981 |
| GB | 2154003 | 8/1985 |
| GB | 2204408 | 11/1988 |
| JP | 54-41191 | 4/1979 |
| JP | 55-10581 | 1/1980 |
| JP | 55-10583 | 1/1980 |
| JP | 55-10584 | 1/1980 |
| JP | 55-12406 | 1/1980 |
| JP | 56-163447 | 12/1981 |
| JP | 57-70448 | 4/1982 |
| JP | 60-173457 | 9/1985 |
| JP | 60-173458 | 9/1985 |
| JP | 60-173459 | 9/1985 |
| JP | 62-114747 | 5/1987 |
| JP | 63-58149 | 3/1988 |
| JP | 63-128252 | 5/1988 |
| JP | 63-139246 | 6/1988 |
| JP | 63-294799 | 12/1988 |
| JP | 63-317758 | 12/1988 |
| JP | 1-114746 | 5/1989 |
| JP | 1-114747 | 5/1989 |
| JP | 1-134244 | 5/1989 |
| JP | 1-156658 | 6/1989 |
| JP | 2-62958 | 3/1990 |
| JP | 2-120655 | 5/1990 |
| JP | 2-287145 | 11/1990 |
| JP | 2-310457 | 12/1990 |
| JP | 3-26956 | 2/1991 |
| JP | 3-28752 | 2/1991 |
| JP | 3-181850 | 8/1991 |
| JP | 3-202764 | 9/1991 |
| JP | 5-72171 | 3/1993 |
| JP | 5-149910 | 6/1993 |
| JP | 5-196595 | 8/1993 |
| JP | 6-118057 | 4/1994 |
| JP | 6-190050 | 7/1994 |
| JP | 6-285855 | 10/1994 |
| JP | 9-189675 | 7/1997 |
| JP | 10-170471 | 6/1998 |
| JP | 10-332626 | 12/1998 |
| JP | 11-108875 | 4/1999 |
| JP | 11-108879 | 4/1999 |
| SU | 1281988 | 1/1987 |
| WO | WO 85/05119 | 11/1985 |
| WO | WO 89/08713 | 9/1989 |
| WO | WO 90/05300 | 5/1990 |
| WO | WO 91/04704 | 4/1991 |
| WO | WO 92/13271 | 8/1992 |
| WO | WO 94/20602 | 9/1994 |
| WO | WO 94/27140 | 11/1994 |
| WO | WO 95/02817 | 1/1995 |
| WO | WO 97/00441 | 1/1997 |
| WO | WO 97/18464 | 5/1997 |
| WO | WO 97/19344 | 5/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | 9835225 | 8/1998 |
| WO | WO 98/43073 | 10/1998 |
| WO | WO 98/58250 | 12/1998 |
| WO | WO 99/05516 | 2/1999 |
| WO | WO 99/08106 | 2/1999 |
| WO | WO 99/30152 | 6/1999 |
| WO | WO 01/33216 A1 * | 5/2001 |

OTHER PUBLICATIONS

Albery, W. J. et al., "Amperometric enzyme electrodes. Part II. Conducting salts as electrode materials for the oxidation of glucose oxidase," J. Electroanal. Chem. Interfacial Electrochem., 194(2) (1 page—Abstract only) (1985).

Albery, W. J. et al., "Amperometric Enzyme Electrodes," Phil. Trans. R. Soc. Lond. B316:107-119 (1987).

Alcock, S. J. et al., "Continuous Analyte Monitoring to Aid Clinical Practice," IEEE Engineering in Medicine and Biology, 319-325 (1994).

Anderson, L. B. et al., "Thin-Layer Electrochemistry: Steady-State Methods of Studying Rate Processes," J. Electroanal. Chem., 10:295-305 (1965).

Bartlett, P. N. et al., "Covalent Binding of Electron Relays to Glucose Oxidation," J. Chem. Soc. Chem. Commun., 1603-1604 (1987).

Bartlett, P. N. et al., "Strategies for the Development of Amperometric Enzyme Electrodes," Biosensors, 3:359-379 (1987/1988).

Bartlett, P. N. et al., "Modification of glucose oxidase by tetrathiafulvalene," J. Chem. Soc., Chem. Commun., 16 (1 page—Abstract only) (1990).

Bobbioni-Harsch, E. et al., "Lifespan of subcutaneous glucose sensors and their performances during dynamic glycaemia changes in rats," J. Biomed. Eng. 15:457-463 (1993).

Brandt, J. et al., "Covalent attachment of proteins to polysaccharide carriers by means of benzoquinone," Biochim. Biophys. Acta, 386(1) (1 page Abstract only) (1975).

Brownlee, M. et al., "A Glucose-Controlled Insulin-Delivery System: Semisynthetic Insulin Bound to Lectin", Science, 206(4423):1190-1191 (Dec. 7, 1979).

Cass, A.E.G. et al., "Ferrocene-Mediated Enzyme Electrode for Amperometric Determination of Glucose", Anal. Chem., 56(4):667-671 (Apr. 1984).

Cass, A.E.G. et al., "Ferricinum Ion As An Electron Acceptor for Oxido-Reductases," J. Electroanal. Chem., 190:117-127 (1985).

Castner, J. F. et al., "Mass Transport and Reaction Kinetic Parameters Determined Electrochemically for Immobilized Glucose Oxidase," Biochemisty, 23(10):2203-2210 (1984).

Chen, C.Y. et al., "Amperometric Needle-Type Glucose Sensor based on a Modified Platinum Electrode with Diminished Response to Interfering Materials", Analytica Chimica Acta, 265:5-14 (1992).

Chen, C.Y. et al., "A Biocompatible Needle-Type Glucose Sensor Based on Platinum-Electroplated Carbon Electrode", Applied Biochemistry and Biotechnology, 36:211-226 (1992).

Claremont, D.J. et al., "Biosensors for Continuous In Vivo Glucose Monitoring", IEEE Engineering in Medicine and Biology Society 10th Annual International Conference, New Orleans, Louisiana, 3 pp. (Nov. 4-7, 1988).

Clark, L.C., Jr. et al., "Electrode Systems for Continuous Monitoring in Cardiovascular Surgery," Annals New York Academy of Sciences, pp. 29-45 (1962).

Clark, L.C. et al., "Differential Anodic Enzyme Polarography for the Measurement of Glucose", Oxygen Transport to Tissue: Instrumentation, Methods, and Physiology, 127-133 (1973).

Clarke, W. L., et al., "Evaluating Clinical Accuracy of Systems for Self-Monitoring of Blood Glucose," Diabetes Care, 10(5):622-628 (Sep.-Oct. 1987).

Csoregi, E. et al., "Design, Characterization, and One-Point in Vivo Calibration of a Subcutaneously Implanted Glucose Electrode," Anal. Chem. 66(19):3131-3138 (Oct. 1, 1994).

Csoregi, E. et al., "On-Line Glucose Monitoring by Using Microdialysis Sampling and Amperometric Detection Based on "Wired" Glucose Oxidase in Carbon Paste," Mikrochim. Acta. 121:31-40 (1995).

Davis, G., "Electrochemical Techniques for the Development of Amperometric Biosensors", Biosensors, 1:161-178 (1985).

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme," J. Phys. Chem., 91(6):1285-1289 (1987).

Degani, Y. et al., "Direct Electrical Communication between Chemically Modified Enzymes and Metal Electrodes. 2. Methods for Bonding Electron-Transfer Relays to Glucose Oxidase and D-Amino-Acid Oxidase," J. Am. Chem. Soc., 110(8):2615-2620 (1988).

Degani, Y. et al., "Electrical Communication between Redox Centers of Glucose Oxidase and Electrodes via Electrostatically and Covalently Bound Redox Polymers," J. Am. Chem. Soc., 111:2357-2358 (1989).

Denisevich, P. et al., "Unidirectional Current Flow and Charge State Trapping at Redox Polymer Interfaces on Bilayer Electrodes: Principles, Experimental Demonstration, and Theory," J. Am. Chem. Soc., 103(16):4727-4737 (1981).

Dicks, J. M., "Ferrocene modified polypyrrole with immobilised glucose oxidase and its application in amperometric glucose microbiosensors," Ann. Biol. clin., 47:607-619 (1989).

Ellis, C. D., "Selectivity and Directed Charge Transfer through an Electroactive Metallopolymer Film," J. Am. Chem. Soc., 103(25):7480-7483 (1981).

Engstrom, R.C., "Electrochemical Pretreatment of Glassy Carbon Electrodes", Anal. Chem., 54(13):2310-2314 (Nov. 1982).

Engstrom, R.C. et al., "Characterization of Electrochemically Pretreated Glassy Carbon Electrodes", Anal. Chem., 56(2):136-141 (Feb. 1984).

Fischer, H. et al., "Intramolecular Electron Transfer Mediated by 4,4'-Bipyridine and Related Bridging Groups", J. Am. Chem. Soc., 98(18):5512-5517 (Sep. 1, 1976).

Foulds, N.C. et al., "Enzyme Entrapment in Electrically Conducting Polymers," J. Chem. Soc., Faraday Trans 1., 82:1259-1264 (1986).

Foulds, N.C. et al., "Immobilization of Glucose Oxidase in Ferrocene-Modified Pyrrole Polymers," Anal. Chem., 609(22):2473-2478 (Nov. 15, 1988).

Frew, J.E. et al., "Electron-Transfer Biosensors", Phil. Trans. R. Soc. Lond., B316:95-106 (1987).

Gernet, S. et al., "Fabrication and Characterization of a Planar Electrochemical Cell and Its Application as a Glucose Sensor", Biosensors & Actuators, 18:59-70 (1989).

Gorton, L. et al., "Selective detection in flow analysis based on the combination of immobilized enzymes and chemically modified electrodes," Analytica Chimica Acta., 250:203-248 (1991).

Gregg, B. A. et al., "Cross-Linked Redox Gels Containing Glucose Oxidase for Amperometric Biosensor Applications", Analytical Chemistry, 62(3):258-263 (Feb. 1, 1990).

Gregg, B. A. et al., "Redox Polymer Films Containing Enzymes. 1. A Redox-Conducting Epoxy Cement: Sythesis, Characterization, and Electrocatalytic Oxidation of Hydroquinone," J. Phys. Chem., 95(15):5970-5975 (1991).

Hale, P.D. et al., "A New Class of Amperometric Biosensor Incorporating a Polymeric Electron-Transfer Mediator," J. Am. Chem. Soc., 111(9):3482-3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", Anal. Chem., 60(19):2002-2007 (Oct. 1, 1988).

Hawkridge, F. M. et al., "Indirect Coulometric Titration of Biological Electron Transport Components," Analytical Chemistry, 45(7):1021-1027 (Jun. 1973).

Heineman, W.R. "Spectro-electro-chemistry", Analytical Chemistry, 50(3):390-392, 394, 396, 398, 400, 402 (Mar. 1978).

Heineman, W.R. et al., "Measurement of Enzyme E.degree. Values by Optically Transparent Thin Layer Electrochemical Cells", Analytical Chemistry, 47(1):79, 82-84 (Jan. 1975).

Heller, A., "Electrical Wiring of Redox Enzymes," Acc. Chem. Res., 23(5):129-134 (1990).

Heller, A., "Electrical Connection of Enzyme Redox Centers to Electrodes," J. Phys. Chem 96(9):3579-3587 (1992).

Heller, A., "Amperometric biosensors based on three-dimensional hydrogel-forming epoxy networks," Sensors and Actuators B, 13-14:180-183 (1993).

Ianniello, R.M. et al., "Differential Pulse Voltammetric Study of Direct Electron Transfer in Glucose Oxidase Chemically Modified Graphite Electrodes", Anal. Chem., 54:(7):1098-1101 (Jun. 1981).

Ianniello, R.M. et al. "Immobilized Enzyme Chemically Modified Electrode as an Amperometric Sensor", Anal. Chem., 53(13):2090-2095 (Nov. 1981).

Ikeda, T. et al., "Glucose oxidase-immobilized benzoquinone-carbon paste electrode as a glucose sensor," Agric. Biol. Chem., 49(2) (1 page—Abstract only) (1985).

Johnson, J. M. et al., "Potential-Dependent Enzymatic Activity in a Enzyme Thin-Layer Cell," Anal. Chem. 54:1377-1383 (1982).

Johnson, K.W., "Reproducible Electrodeposition of Biomolecules for the Fabrication of Miniature Electroenzymatic Biosensors", Sensors and Actuators B Chemical, B5:85-89 (1991).

Johnson K. W. et al., "In Vivo Evaluation of an Electroenzymatic Glucose Sensor Implanted in Subcutaneous Tissue", Biosensors & bioelectronics 7:709-714 (1992).

Jonsson, G. et al., "An Amperometric Glucose Sensor Made by Modification of a Graphite Electrode Surface With Immobilized Glucose Oxidase and Adsorbed Mediator", Biosensors, 1:35-368 (1985).

Josowicz, M. et al., "Electrochemical Pretreatment of Thin Film Platinum Electrodes", J. Elecrochem. Soc., 135(1):112-115 (Jan. 1988).

Katakis, I. et al., "L-.alpha.-Glycerophosphate and L-Lactate Electrodes Based on the Electrochemical "Wiring" of Oxidases," Analytical Chemistry, 64(9):1008-1013 (May 1, 1992).

Katakis, I. et al., "Electrostatic Control of the Electron Transfer Enabling Binding of Recombinant Glucose Oxidase and Redox Polyelectrolytes," J. Am. Chem. Soc., 116(8):3617-3618 (1994).

Kenausis, G. et al., "'Wiring' of glucose oxidase and lactate oxidase within a hydrogel made with poly(vinyl pyridine) complexed with [Os(4,4'-dimethoxy-2,2'-bipyridine).sub.2 C1].sup.+/2+," J. Chem. Soc., Faraday Trans., 92(20):4131-4136 (1996).

Kondo, T. et al., "A Miniature Glucose Sensor, Implantable in the Blood Stream", Diabetes Care, 5(3):218-221 (May-Jun. 1982).

Kulys, J. et al., "Mediatorless peroxidase electrode and preparation of bienzyme sensors," Bioelectrochemistry and Bioenergetics, 24:305-311 (1990).

Lager, W. et al., "Implantable Electrocatalytic Glucose Sensor," Horm. Metab. Res., 26:526-530 (Nov. 1994).

Lee, J. et al., "A New Glucose Sensor using Microporous Enzyme Membrane", Sensors and Actuators, B3:215-219 (1991).

Lewandowski, J.J. et al., "Evaluation of a Miniature Blood Glucose Sensor", Trans Am Soc Artif Intern Organs, XXXIV: 255-258 (1988).

Lindner, E. et al. "Flexible (Kapton-Based) Microsensor Arrays of High Stability for Cardiovascular Applications", J. Chem. Soc. Faraday Trans., 89(2):361-367 (Jan. 21, 1993).

Maidan, R. et al., "Elimination of Electrooxidizable Interferant-Produced Currents in Amperometric Biosensros," Analytical Chemistry, 64(23):2889-2896 (Dec. 1, 1992).

Mann-Buxbaum, E. et al, "New Microminiaturized Glucose Sensors Using Covalent Immobilization Techniques", Sensors and Actuators, B1:518-522 (1990).

Mastrototaro, J.J. et al., "An Electroenzymatic Glucose Sensor Fabricated on a Flexible Substrate", Sensors and Biosensors B Chemical, B5:139-144 (1991).

Matthews, D.R., et al., "An Amperometric Needle-Type Glucose Sensor Tested in Rats and Man", Original Articles, pp. 248-252 (1988).

McKean et al., "A telemetry-Instrumentation System for Chronically Implanted Glucose and Oxygen Sensors", IEEE Transactions of Biomedical Engineering, 35(7):526-532 (Jul. 1988).

McNeil, C. J. et al., "Thermostable Reduced Nicotinamide Adenine Dinucleotide Oxidase: Application to Amperometric Enzyme Assay," Anal. Chem., 61(1):25-29 (Jan. 1, 1989).

Miyawaki, O. et al., "Electrochemical and Glucose Oxidase Coenzyme Activity of Flavin Adenine Dinucleotide Covalently Attached to Glassy Carbon at the Adenine Amino Group", Biochimica et Biophysica Acta, 838:60-68 (1985).

Moatti-Sirat, D. et al., "Evaluating in vitro and in vivo the inteference of ascorbate and acetaminophen on glucose detection by a needle-type glucose sensor," Biosensors & Bioelectronics, 7(5):345-352 (1992).

Moatti-Sirat, D. et al., "Towards continuous glucose monitoring: in vivo evaluation of a miniaturized glucose sensor implanted for several days in rat subcutaneous tissue," Diabetologia, 35(3) (1 page—Abstract only) (Mar. 1992).

Moatti-Sirat, D. et al., "Reduction of acetaminophen interference in glucose sensors by a composite Nafion membrane: demonstration in rats and man," Diabetologia, 37(6) (1 page—Abstract only) (Jun. 1994).

Moser, I. et al., "Advanced Immobilization and Protein Techniques on thin Film Biosensors", Sensors and Actuators, B7:356-362 (1992).

Moussy, F. et al., "Performance of Subcutaneously Implanted Needle-Type Glucose Sensors Employing a Novel Trilayer Coating", Anal. Chem., 65:2072-2077 (1993).

Nagy, G. et al., "A New Type of Enzyme Electrode: The Ascorbic Acid Eliminator Electrode," Life Sciences, 31(23):2611-2616 (1982).

Nakamura, S. et al., "Effect of Periodate Oxidation on the Structure and Properties of Glucose Oxidase," Biochimica et Biophysica Acta., 445:294-308 (1976).

Narazimhan, K. et al., "p-Benzoquinone activation of metal oxide electrodes for attachment of enzymes," Enzyme Microb. Technol., 7(6) (1 page—Abstract only) (1985).

Ohara, T. J. et al., "Glucose Electrodes Based on Cross-Linked [Os(bpy)$_2$Cl]$^{+/2+}$ Complexed Poly(1-vinylimadazole) Films," Analytical Chemistry, 65(23):3512-3516 (Dec. 1, 1993).

Ohara, T. J. et al., ""Wired" Enzyme Electrodes for Amperometric Determination of Glucose or Lactate in the Presence of Interfering Substances," Analytical Chemistry, 66(15):2451-2457 (Aug. 1, 1994).

Ohara, T. J., "Osmium Bipyridyl Redox Polymers Used in Enzyme Electrodes," Platinum Metals Rev., 39(2):54-62 (Apr. 1995).

Olievier, C. N. et al., "In vivo Measurement of Carbon Dioxide Tension with a Miniature Electrode," Pflugers Arch. 373:269-272 (1978).

Paddock, R. et al., "Electrocatalytic reduction of hydrogen peroxide via direct electron transfer from pyrolytic graphite electrodes to irreversibly adsorbed cytochrome c peroxidase," J. Electroanal. Chem., 260:487-494 (1989).

Palleschi, G. et al., "A Study of Interferences in Glucose Measurements in Blood by Hydrogen Peroxide Based Glucose Probes", Anal. Biochem., 159:114-121 (1986).

Palleschi, G. et al., "Ideal Hydrogen Peroxide-Based Glucose Sensor", Applied Biochemistry and Biotechnology, 31:21-35 (1991).

Pankratov, I. et al., "Sol-gel derived renewable-surface biosensors," Journal of Electroanalytical Chemistry, 393:35-41 (1995).

Pathak, C. P. et al., "Rapid Photopolymerization of Immunoprotective Gels in Contact with Cells and Tissue," J. Am. Chem. Soc., 114(21):8311-8312 (1992).

Pickup, J. et al., "Potentially-implantable amperometric glucose sensors with mediated electron transfer: improving the operating stability," Biosensors, 4(2) (1 page—Abstract only) (1989).

Pishko, M.V. et al., "Amperometric Glucose Microelectrodes Prepared Through Immobilization of Glucose Oxidase in Redox Hydrogels", Anal. Chem., 63(20):2268-2272 (Oct. 15, 1991).

Poitout, V. et al., "In vitro and in vivo evaluation in dogs of a miniaturized glucose sensor," ASAIO Transactions, 37(3) (1 page—Abstract only) (Jul.-Sep. 1991).

Poitout, V. et al., "Calibration in dogs of a subcutaneous miniaturized glucose sensor using a glucose meter for blood glucose determination," Biosensors & Bioelectronics, 7:587-592 (1992).

Poitout, V. et al., "A glucose monitoring system for on line estimation in man of blood glucose concentration using a miniaturized glucose sensor implanted in the subcutaneous tissue and a wearable control unit," Diabetolgia, 36(7) (1 page—Abstract only) (Jul. 1993).

Pollak, A. et al., "Enzyme Immobilization by Condensation Copolymerization into Cross-Linked Polyacrylamide Gels," J. Am. Chem. Soc., 102(20):6324-6336 (1980).

Pons, B. S. et al., "Application of Deposited Thin Metal Films as Optically Transparent Electrodes for Internal Reflection Spectrometric Observation of Electrode Solution Interfaces", Analytical Chemistry, 39(6):685-688, (May 1967).

Reach, G. et al., "A Method for Evaluating in vivo the Functional Characteristics of Glucose Sensors", Biosensors 2:211-220 (1986).

Reach, G. et al., "Can Continuous Glucose Monitoring Be Used for the Treatment of Diabetes?" Analytical Chemistry, 64(6):381-386 (Mar. 15, 1992).

Rebrin, K. et al., "Automated Feedback Control of Subcutaneous Glucose Concentration in Diabetic Dogs", Diabetologia, 32(8):573-576 (Aug. 1989).

Sasso, S.V. et al., "Electropolymerized 1,2-Diaminobenzene as a Means to Prevent Interferences and Fouling and to Stabilize Immobilized Enzyme in Electrochemical Biosensors", Anal. Chem., 62(11): 1111-1117 (Jun. 1, 1990).

Schalkhammer, T. et al., "Electrochemical Glucose Sensors on Permselective Non-conducting Substituted Pyrrole Polymers", Sensors and Actuators, B4:273-281 (1991).

Scheller, F. et al., "Enzyme electrodes and their application," Phil. Trans. R. Soc. Lond., B 316:85-94 (1987).

Shichiri, M. et al., "Glycemic Control in Pancreatectomized Dogs with a Wearable Artificial Endocrine Pancreas", Diabetologia, 24(3):179-184 (Mar. 1983).

Shigeru, T. et al, "Simultaneous Determination of Glucse and 1,5-=Anydroglucitol", Chemical Abstracts, 111:394 (1989).

Sittampalam, G. et al., "Surface-Modified Electrochemical Detector for Liquid Chromatography", Anal. Chem., 55(9):1608-1610 (Aug. 1983).

Soegijoko, S. et al., Horm. Metabl. Res., Suppl. Ser, 12 (1 page—Abstract only) (1982).

Sprules, S. D. et al., "Evaluation of a New Disposable Screen-Printed Sensor Strip for the Measurement of NADH and Its Modification to Produce a Lactate Biosensor Employing Microliter Volumes," Electroanalysis, 8(6):539-543 (1996).

Sternberg, R. et al., "Covalent Enzyme Coupling on Cellulose Acetate Membranes for Glucose Sensor Development," Analytical Chemistry, 60(24):2781-2786 (Dec. 15, 1988).

Sternberg, F. et al., "Calibration Problems of Subcutaneous Glucosensors when Applied "In-Situ" in Man," Norm. metabl. Res, 26:523-525 (1994).

Suekane, M., "Immobilization of glucose isomerase," Zeitschrift fur Allgemeine Mikrobiologie, 22(8):565-576 (1982).

Tarasevich, M.R. "Bioelectrocatalysis", Comprehensive Treatise of Electrochemistry, 10 (Ch. 4):231-295 (1985).

Taylor, C. et al., "'Wiring' of glucose oxidase within a hydrogel made with polyvinyl imidazole complexed with [(Os-4,4'-dimethoxy-2,2'-bipyridine)Cl]$^{+/2+}$," Journal of Electroanalytical Chemistry, 396:511-515 (1995).

Trojanowicz, M. et al., "Enzyme Entrapped Polypyrrole Modified Electrode for Flow-Injection Determination of Glucose," Biosensors & Bioelectronics, 5:149-156 (1990).

Turner, A.P.F. et al., "Diabetes Mellitus: Biosensors for Research and Management", Biosensors, 1:85-115 (1985).

Turner, R. F. B. et al., "A Biocompatible Enzyme Electrode for Continuous in vivo Glucose Monitoring in Whole Blood," Sensors and Actuators, B1(1-6):561-564 (Jan. 1990).

Umaha, M., "Protein-Modified Electrochemically Active Biomaterial Surface," U.S. Army Research Office Report, (12 pages) (Dec. 1988).

Urban, G. et al., "Miniaturized Thin-Film Biosensors Using Covalently Immobilized Glucose Oxidase", Biosensors & Bioelectronics, 6(7):555-562 (1991).

Velho, G. et al., "Strategies for calibrating a subcutaneous glucose sensor," Biomed. Biochin. Acta, 48(11/12):957-964 (1989).

Von Woedtke, T. et al., "In Situ Calibration of Implanted Electrochemical Glucose Sensors," Biomed. Biochim. Acta, 48(11/12):943-952 (1989).

Vreeke, M. et al., "Hydrogen Peroxide and .beta.-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network," Analytical Chemistry, 64(24):3084-3090 (Dec. 15, 1992).

Vreeke, M. S. et al., "Chapter 15: Hydrogen Peroxide Electrodes Based on Electrical Connection of Redox Centers of Various Peroxidases to Electrodes through a Three-Dimensional Electron Relaying Polymer Network," Diagnostic Biosensor Polymers, 7 pp. (Jul. 26, 1993).

Wang, J. et al., "Activation of Glassy Carbon Electrodes by Alternating Current Electrochemical Treatment", Analytica Chimica Acta, 167:325-334 (Jan. 1985).

Wang, J. et al., "Amperometric biosensing of organic peroxides with peroxidase-modified electrodes," Analytica Chimica Acta. 254:81-88 (1991).

Wang, J. et al., "Screen-Printable Sol-Gel Enzyme-Containing Carbon Inks," Analytical Chemistry, 68(15):2705-2708 (Aug. 1, 1996).

Wang, J. et al., "Sol-Gel-Derived Metal-Dispersed Carbon Composite Amperometric Biosensors," Electroanalysis, 9(1):52-55 (1997).

Williams, D.L. et al., "Electrochemical-Enzymatic Analysis of Blood Glucose and Lactate", Anal. Chem., 42(1):118-121 (Jan. 1970).

Yabuki, S. et al., "Electro-conductive Enzyme Membrane," J. Chem. Soc. Chem. Commun, 945-946 (1989).

Yamasaki, Y., "The Development of a Needle-Type Glucose Sensor for Wearable Artificial Endocrine Pancreas", Medical Journal of Osaka University, vol. 35, No. 1-2, pp. 24-34 (Sep. 1994).

Yang, L. et al., "Determination of Oxidase Enzyme Substrates Using Cross-Flow Thin-Layer Amperometry," Electroanalysis, 8(8-9):716-721 (1996).

Yao, T. et al., "A Chemically-Modified Enzyme Membrane Electrode As an Amperometric Glucose Sensor," Analytica Chimica Acta., 148:27-33 (1983).

Yao, S.J. et al., "The Interference of Ascorbate and Urea in Low-Potential Electrochemical Glucose Sensing", Proceedings of the Twelfth Annual International Conference of the IEEE Engineering in Medicine and Biology Society, 12(2):487-489 (Nov. 1-4, 1990).

Ye, L. et al., "High Current Density "Wired" Quinoprotein Glucose Dehydrogenase Electrode," Anal. Chem., 65(3):238-241 (Feb. 1, 1993).

Yildiz, A., "Evaluation of an Improved Thin-Layer Electrode", Analytical Chemistry, 40(7):1018-1024 (Jun. 1968).

Zamzow, K., et al., New Wearable Continuous Blood Glucose Monitor (BGM) and Artificial Pancreas (AP), Diabetes, 39:5A(20) (May 1990).

* cited by examiner

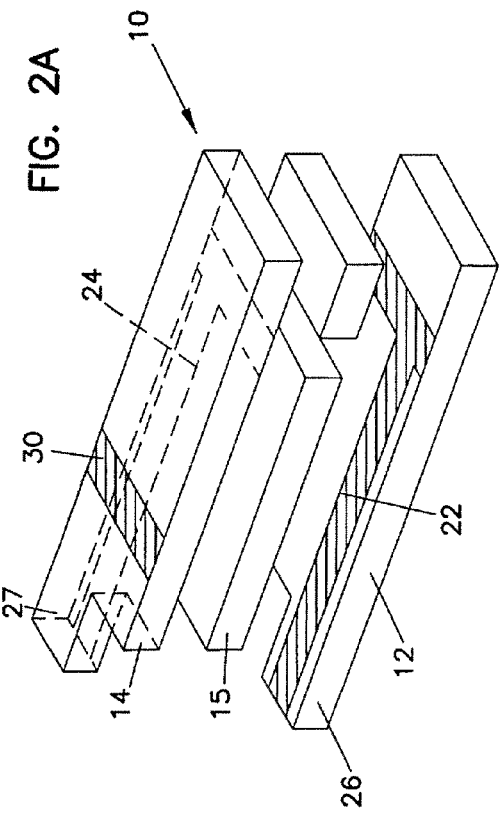
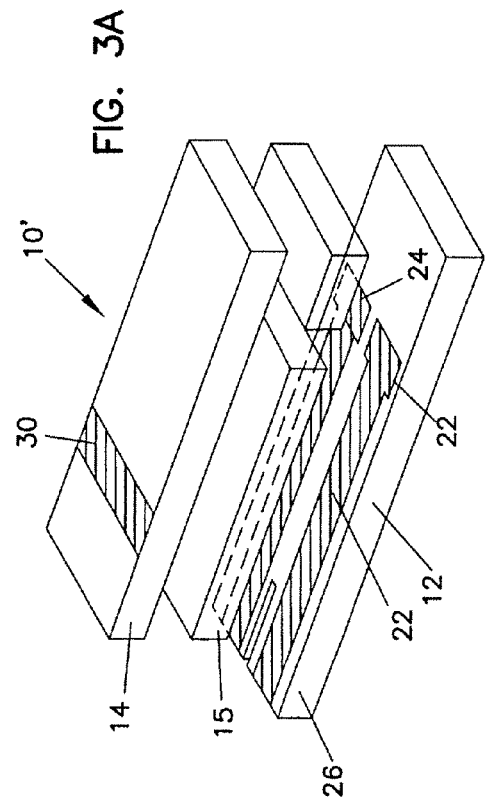
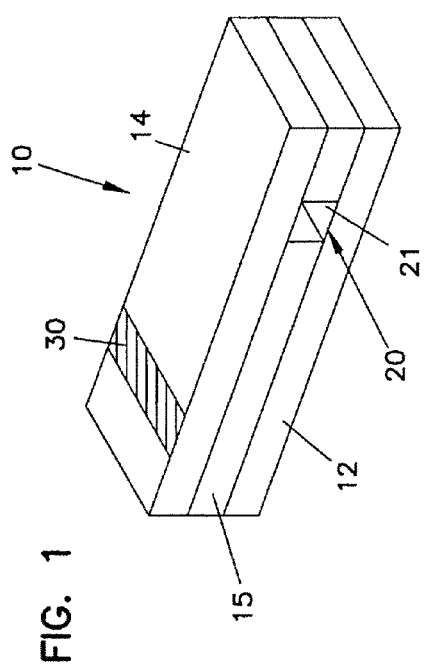
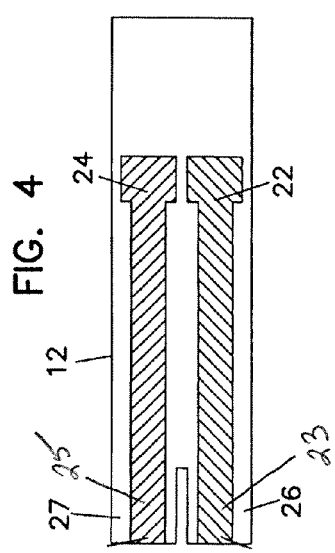

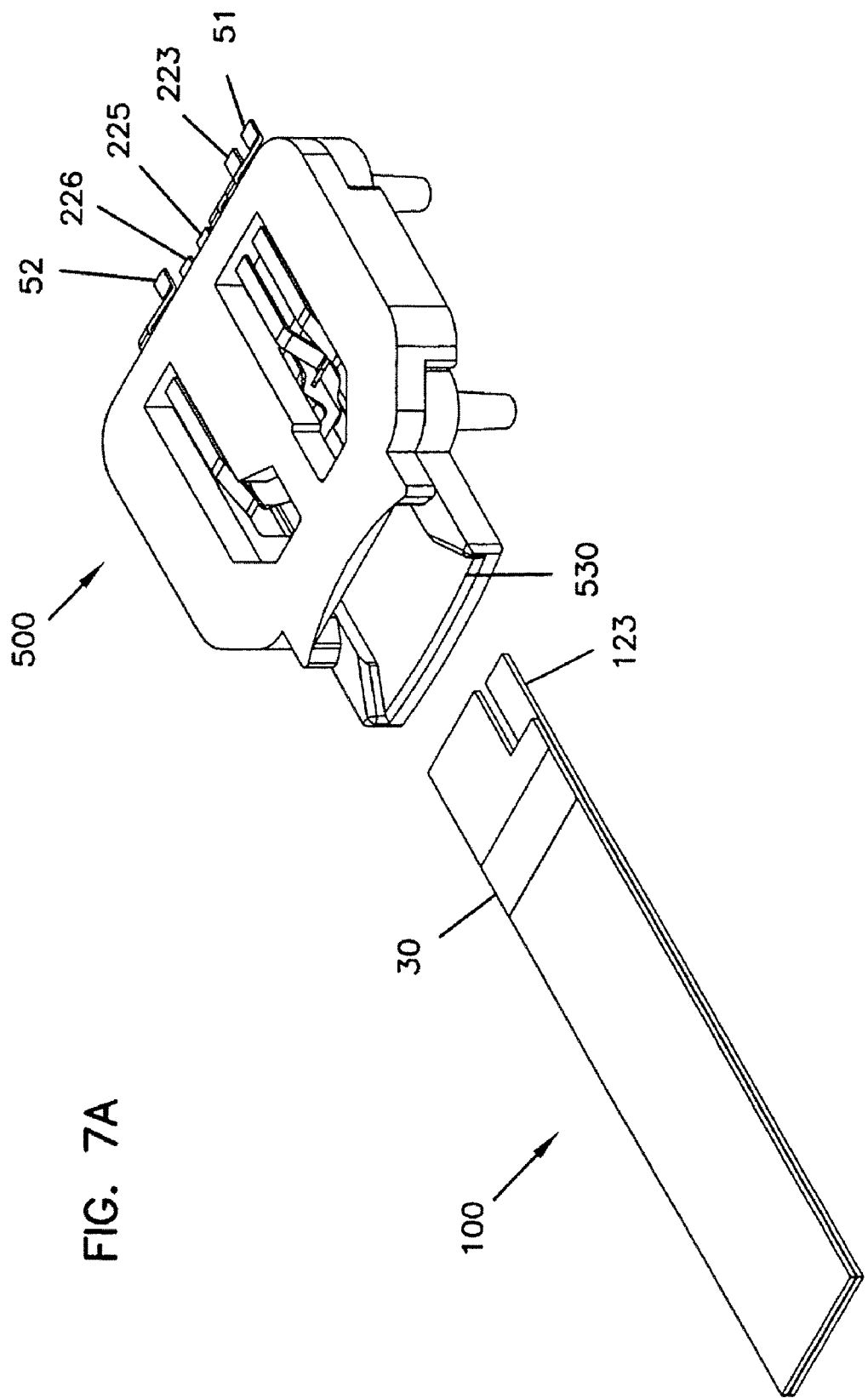

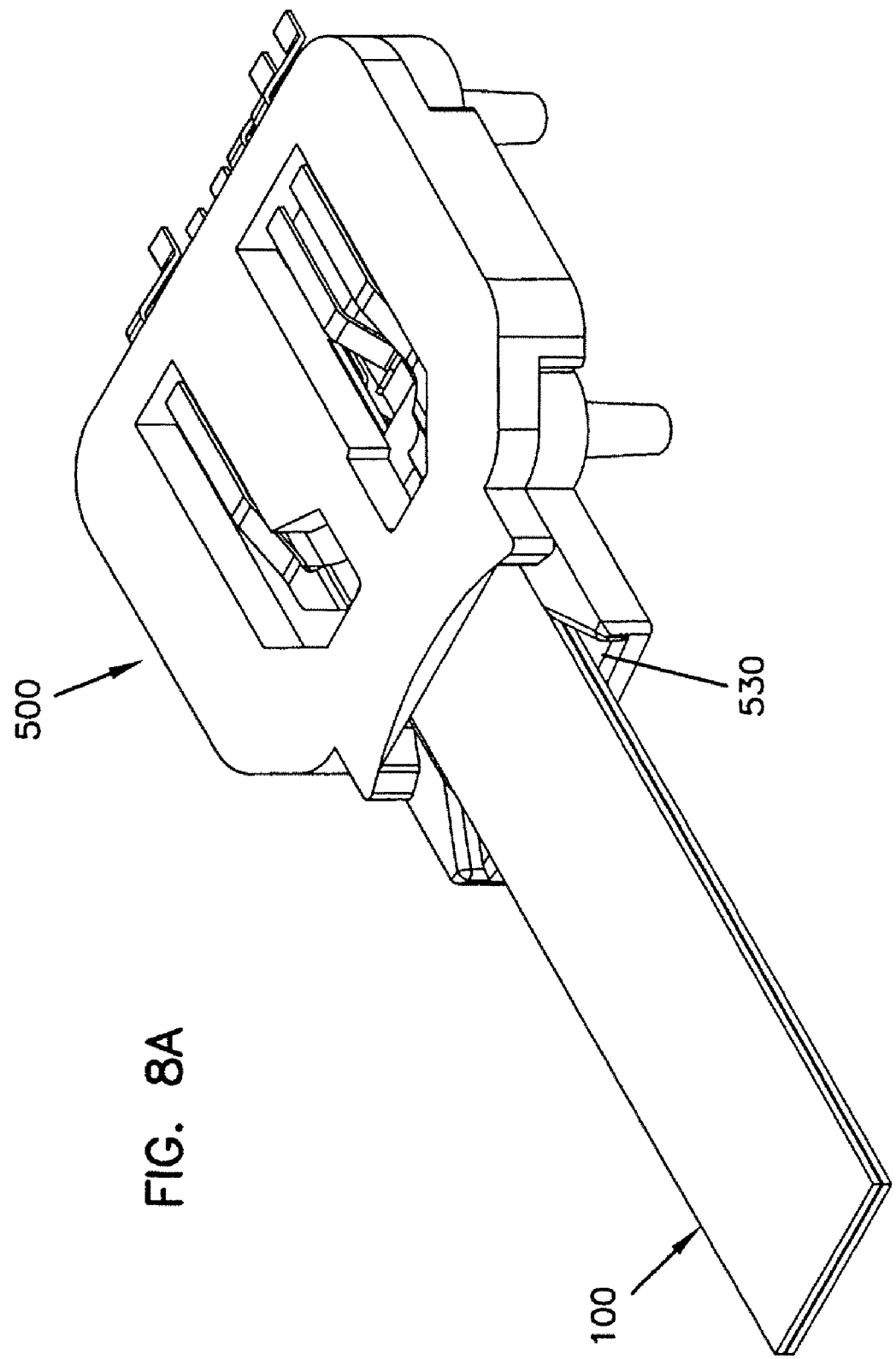

US 8,066,858 B2

ANALYTE SENSOR WITH INSERTION MONITOR, AND METHODS

This application is a continuation of U.S. Ser. No. 11/281,883, filed Nov. 17, 2005, which is a continuation-in-part of U.S. Ser. No. 10/866,477, filed Jun. 12, 2004 now abandoned, which is a continuation of U.S. Ser. No. 10/033,575, filed Dec. 28, 2001, issued as U.S. Pat. No. 6,749,740, which is a continuation of U.S. Ser. No. 09/434,026, filed Nov. 4, 1999, issued as U.S. Pat. No. 6,616,819, the entire disclosures of which are incorporated herein by reference.

FIELD OF THE INVENTION

This invention relates to analytical sensors for the detection of bioanalytes in a small volume sample, and methods of making and using the sensors.

BACKGROUND

Analytical sensors are useful in chemistry and medicine to determine the presence and concentration of a biological analyte. Such sensors are needed, for example, to monitor glucose in diabetic patients and lactate during critical care events.

Currently available technology measures bioanalytes in relatively large sample volumes, e.g., generally requiring 3 microliters or more of blood or other biological fluid. These fluid samples are obtained from a patient, for example, using a needle and syringe, or by lancing a portion of the skin such as the fingertip and "milking" the area to obtain a useful sample volume. These procedures are inconvenient for the patient, and often painful, particularly when frequent samples are required. Less painful methods for obtaining a sample are known such as lancing the arm or thigh, which have a lower nerve ending density. However, lancing the body in the preferred regions typically produces submicroliter samples of blood, because these regions are not heavily supplied with near-surface capillary vessels.

It would therefore be desirable and very useful to develop a relatively painless, easy to use blood analyte sensor, capable of performing an accurate and sensitive analysis of the concentration of analytes in a small volume of sample.

It would also be desirable to develop methods for manufacturing small volume electrochemical sensors capable of decreasing the errors that arise from the size of the sensor and the sample.

SUMMARY OF THE DISCLOSURE

The sensors of the present invention provide a method for the detection and quantification of an analyte. In general, the invention includes a method and sensor for analysis of an analyte in a sample, e.g., a small volume sample, by, for example, coulometry, amperometry and/or potentiometry. A sensor of the invention may utilize a non-leachable or diffusible electron transfer agent and/or a redox mediator. The sensor also includes a sample chamber to hold the sample in electrolytic contact with the working electrode.

In one embodiment, the working electrode faces a counter electrode, forming a measurement zone within the sample chamber, between the two electrodes, that is sized to contain no more than about 1 μL of sample, e.g., no more than about 0.5 μL, e.g., no more than about 0.32 μL, e.g., no more than about 0.25 μL, e.g., no more than about 0.1 μL of sample.

In one embodiment of the invention, a sensor, configured for insertion into an electronic meter, is provided with a working electrode and a counter electrode, and a conductive insertion monitor which provides electrical contact with the electronic meter if the sensor is properly inserted into the meter. The conductive insertion monitor is configured and arranged to close an electrical circuit when the sensor is properly inserted into the electronic connector.

In another embodiment of the invention, a sensor is provided with a plurality of contacts, each contact having a contact pad, which is a region for connection with an electronic meter. The plurality of contacts and contact pads are on a substrate having a length and a width, and each contact pad has a contact pad width taken parallel to the width of the substrate. The sum of the contact pad widths is greater than the width of the substrate. In one embodiment, six electrical connections are made with six contact pads on the sensor but in a width that is approximately the width of four contact pads. For example, a working electrode, three counter electrodes (e.g., one counter electrode and two indicator electrodes), and two insertion trace connections each have a contact pad; connection can be made to each of these six contact pads in the same width of the contact pads of the working electrode and three counter electrodes.

The present invention also includes an electrical connector, for providing electrical contact between a sensor and an electrical meter or other device. The electrical connector has a plurality of contact structures, each which has a proximal contact end for electrical connection to a sensor contact, and a distal end for electrical connection to the electrical device. In one embodiment, a plurality of first contact structures extend longitudinally parallel from the distal to the proximal end. Additionally, one or more second contract structures extend longitudinally next to the first contact structures, from the distal end past the proximal end of the first contact structures, and angle toward a longitudinal center line of the connector. Contact to the sensor is then made via the proximal contact ends.

In some embodiments, the electrical connector has at least two second contact structures extending longitudinally past the proximal end of the first contact structures and angling toward the longitudinal center line of the connector. After the angled or bent portion, the proximal contact ends of the second contact structures of one embodiment make electrical contact with a single conductive surface of a sensor, such as a conductive insertion monitor. In another aspect, the first contact structures can be configured and arranged to contact one or more working and/or counter electrodes of a sensor, and the second contact structures are configured and arranged to contact one or more conductive insertion monitors.

The sensors of the present invention can be configured for side-filling or tip-filling. In addition, in some embodiments, the sensor may be part of an integrated sample acquisition and analyte measurement device. The integrated sample acquisition and analyte measurement device can include the sensor and a skin piercing member, so that the device can be used to pierce the skin of a user to cause flow of a fluid sample, such as blood, that can then be collected by the sensor. In at least some embodiments, the fluid sample can be collected without moving the integrated sample acquisition and analyte measurement device.

In one embodiment, the sensor is connected with an electrical device, to provide a processor coupled to the sensor. The processor is configured and arranged to determine, during electrolysis of a sample in the sample chamber, a series of current values. The processor determines a peak current value from the series of current values. After the current values decrease below a threshold fraction of the peak current values, slope values are determined from the current values and represent a linear function of the logarithm of current values over time. The processor determines, from the slope values, an extrapolation slope. From the extrapolated slope and the measured current values, the processor determines an amount of charge needed to electrolyze the sample and, from that amount of charge, the concentration of the analyte in the sample.

One method of forming a sensor, as described above, includes forming at least one working electrode on a first substrate and forming at least one counter or counter/reference electrode on a second substrate. A spacer layer is disposed on either the first or second substrates. The spacer layer defines a chamber into which a sample can be drawn and held when the sensor is completed. A redox mediator and/or second electron transfer agent can be disposed on the first or second substrate in a region that will be exposed within the sample chamber when the sensor is completed. The first and second substrates are then brought together and spaced apart by the spacer layer with the sample chamber providing access to the at least one working electrode and the at least one counter or counter/reference electrode. In some embodiments, the first and second substrates are portions of a single sheet or continuous web of material. The invention includes particularly efficient and reliable methods for the manufacture of these sensors.

One such efficient and reliable method includes providing an adhesive having first and second surfaces covered with first and second release liners and then making detailed cuts through the first release liner and the adhesive but not through the second release liner. These cuts define one or more sample chamber regions. A portion of the first release liner is removed to expose a portion of the first adhesive surface, which leaves a remaining portion of the first release liner over the sample chamber regions. This exposed first adhesive surface is applied to a first substrate having one or more conductive traces disposed thereon. The second release liner is removed together with the adhesive and the first release liner of the sample chamber regions in order to expose the second adhesive surface. The second adhesive surface is then applied to a second substrate having one or more conductive traces disposed thereon. This method forms a sensor having a sample chamber corresponding to one of the sample chamber regions.

These and various other features which characterize the invention are pointed out with particularity in the attached claims. For a better understanding of the invention, its advantages, and objectives obtained by its use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views:

FIG. 1 is a schematic view of a first embodiment of a sensor strip in accordance with the present invention;

FIG. 2A is an exploded view of the sensor strip shown in FIG. 1, the layers illustrated individually with the electrodes in a first configuration;

FIG. 3A is a schematic view of a second embodiment of a sensor strip in accordance with the present invention, the layer illustrated individually with the electrodes in a second configuration;

FIG. 4 is a top view of the first substrate of the sensor strip of FIGS. 3A and 3B;

FIG. 7A is a top perspective view of a sensor strip positioned for insertion within an electrical connector device in accordance with the present invention;

FIG. 8A is a top perspective view of a sensor strip fully positioned within the electrical connector device of FIG. 7A;

DETAILED DESCRIPTION OF THE PREFERRED EMBODIMENT

Figure 2B:
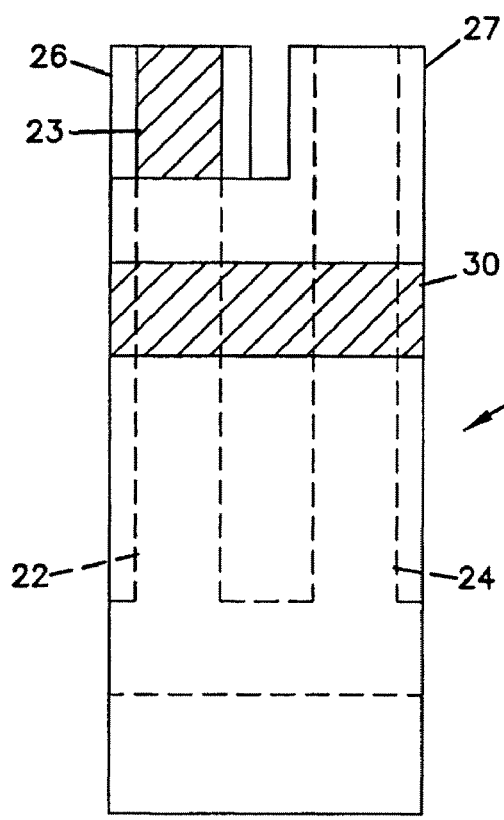
FIG. 2B is a top view of the sensor strip shown in FIGS. 1 and 2A.

As used herein, the following definitions define the stated term:

"Amperometry" includes steady-state amperometry, chronoamperometry, and Cottrell-type measurements.

A "biological fluid" is any body fluid in which the analyte can be measured, for example, blood (which includes whole blood and its cell-free components, such as, plasma and serum), interstitial fluid, dermal fluid, sweat, tears, urine and saliva.

"Coulometry" is the determination of charge passed or projected to pass during complete or nearly complete electrolysis of the analyte, either directly on the electrode or through one or more electron transfer agents. The charge is determined by measurement of charge passed during partial or nearly complete electrolysis of the analyte or, more often, by multiple measurements during the electrolysis of a decaying current and elapsed time. The decaying current results from the decline in the concentration of the electrolyzed species caused by the electrolysis.

A "counter electrode" refers to one or more electrodes paired with the working electrode, through which passes an electrochemical current equal in magnitude and opposite in sign to the current passed through the working electrode. The term "counter electrode" is meant to include counter electrodes which also function as reference electrodes (i.e. a counter/reference electrode) unless the description provides that a "counter electrode" excludes a reference or counter/reference electrode.

An "electrochemical sensor" is a device configured to detect the presence of and/or measure the concentration of an analyte via electrochemical oxidation and reduction reactions. These reactions are transduced to an electrical signal that can be correlated to an amount or concentration of analyte.

"Electrolysis" is the electrooxidation or electroreduction of a compound either directly at an electrode or via one or more electron transfer agents (e.g., redox mediators and/or enzymes).

The term "facing electrodes" refers to a configuration of the working and counter electrodes in which the working surface of the working electrode is disposed in approximate opposition to a surface of the counter electrode. In at least some instances, the distance between the working and counter electrodes is less than the width of the working surface of the working electrode.

An "indicator electrode" or "fill indicator electrode" is an electrode that detects partial or complete filling of a sample chamber and/or measurement zone with sample.

A "layer" is one or more layers.

The "measurement zone" is defined herein as a region of the sample chamber sized to contain only that portion of the sample that is to be interrogated during an analyte assay.

A "non-diffusible," "non-leachable," or "non-releasable" compound is a compound which does not substantially diffuse away from the working surface of the working electrode for the duration of the analyte assay.

A "redox mediator" is an electron transfer agent for carrying electrons between the analyte and the working electrode, either directly or through another electron transfer agent.

A "reference electrode" includes a reference electrode that also functions as a counter electrode (i.e., a counter/reference electrode) unless the description provides that a "reference electrode" excludes a counter/reference electrode.

A "working electrode" is an electrode at which analyte is electrooxidized or electroreduced with or without the agency of a redox mediator.

Referring to the Drawings in general and FIGS. 1 and 2A in particular, a first embodiment of a sensor strip 10 is schematically illustrated. Sensor strip 10 has a first substrate 12, a second substrate 14, and a spacer 15 positioned therebetween. Sensor strip 10 includes at least one working electrode 22 and at least one counter electrode 24. Sensor strip 10 also includes insertion monitor 30.

Sensor Strips

Referring to FIGS. 1, 2A and 2B in particular, sensor strip 10 has first substrate 12, second substrate 14, and spacer 15 positioned therebetween. Sensor strip 10 includes working electrode 22, counter electrode 24 and insertion monitor 30. Sensor strip 10 is a layered construction, in certain embodiments having a generally rectangular shape, i.e., its length is longer than its width, although other shapes are possible as well. Sensor strip 10' of FIGS. 3A, 3B and 4 also has first substrate 12, second substrate 14, spacer 15, working electrode 22, counter electrode 24 and insertion monitor 30.

The dimensions of a sensor may vary. In certain embodiments, the overall length of sensor strip 10, 10' may be no less than about 20 mm and no greater than about 50 mm. For example, the length may be between about 30 and 45 mm; e.g., about 30 to 40 mm. It is understood, however that shorter and longer sensor strips 10, 10' could be made. In certain embodiments, the overall width of sensor strip 10, 10' may be no less than about 3 mm and no greater than about 15 mm. For example, the width may be between about 4 and 10 mm, about 5 to 8 mm, or about 5 to 6 mm. In one particular example, sensor strip 10, 10' has a length of about 32 mm and a width of about 6 mm. In another particular example, sensor strip 10, 10' has a length of about 40 mm and a width of about 5 mm.

In yet another particular example, sensor strip 10, 10' has a length of about 34 mm and a width of about 5 mm.

Substrates

As provided above, sensor strip 10, 10' has first and second substrates 12, 14, non-conducting, inert substrates which form the overall shape and size of sensor strip 10, 10'. Substrates 12, 14 may be substantially rigid or substantially flexible. In certain embodiments, substrates 12, 14 are flexible or deformable. Examples of suitable materials for substrates 12, 14 include, but are not limited, to polyester, polyethylene, polycarbonate, polypropylene, nylon, and other "plastics" or polymers. In certain embodiments the substrate material is "Melinex" polyester. Other non-conducting materials may also be used.

Spacer Layer

As indicated above, positioned between substrate 12 and substrate 14 can be spacer 15 to separate first substrate 12 from second substrate 14. Spacer 15 is an inert non-conducting substrate, typically at least as flexible and deformable (or as rigid) as substrates 12, 14. In certain embodiments, spacer 15 is an adhesive layer or double-sided adhesive tape or film. Any adhesive selected for spacer 15 should be selected to not diffuse or release material which may interfere with accurate analyte measurement.

In certain embodiments, the thickness of spacer 15 may be at least about 0.01 mm (10 µm) and no greater than about 1 mm or about 0.5 mm. For example, the thickness may be between about 0.02 mm (20 µm) and about 0.2 mm (200 µm). In one certain embodiment, the thickness is about 0.05 mm (50 µm), and about 0.1 mm (100 µm) in another embodiment.

Sample Chamber

The sensor includes a sample chamber for receiving a volume of sample to be analyzed; in the embodiment illustrated, particularly in FIG. 1, sensor strip 10, 10' includes sample chamber 20 having an inlet 21 for access to sample chamber 20. In the embodiments illustrated, sensor strips 10, 10' are side-fill sensor strips, having inlet 21 present on a side edge of strips 10, 10'. Tip-fill sensors can also be configured in accordance with this invention.

Sample chamber 20 is configured so that when a sample is provided in chamber 20, the sample is in electrolytic contact with both the working electrode and the counter electrode, which allows electrical current to flow between the electrodes to effect the electrolysis (electrooxidation or electroreduction) of the analyte.

Sample chamber 20 is defined by substrate 12, substrate 14 and spacer 15; in many embodiments, sample chamber 20 exists between substrate 12 and substrate 14 where spacer 15 is not present. Typically, a portion of spacer 15 is removed to provide an area between substrates 12, 14 without spacer 15; this volume of removed spacer is sample chamber 20. For embodiments that include spacer 15 between substrates 12, 14, the thickness of sample chamber 20 is generally the thickness of spacer 15.

Sample chamber 20 has a volume sufficient to receive a sample of biological fluid therein. In some embodiments, such as when sensor strip 10, 10' is a small volume sensor, sample chamber 20 has a volume that is preferably no more than about 1 µL, for example no more than about 0.5 µL, and also for example, no more than about 0.25 µL. A volume of no more than about 0.1 µL is also suitable for sample chamber 20, as are volumes of no more than about 0.05 µL and about 0.03 µL.

A measurement zone is contained within sample chamber 20 and is the region of the sample chamber that contains only that portion of the sample that is interrogated during the analyte assay. In some designs, the measurement zone has a volume that is approximately equal to the volume of sample chamber 20. In some embodiments the measurement zone includes 80% of the sample chamber, 90% in other embodiments, and about 100% in yet other embodiments.

As provided above, the thickness of sample chamber 20 corresponds typically to the thickness of spacer 15. Particularly for facing electrode configurations, this thickness is small to promote rapid electrolysis of the analyte, as more of the sample will be in contact with the electrode surface for a given sample volume. In addition, a thin sample chamber 20 helps to reduce errors from diffusion of analyte into the measurement zone from other portions of the sample chamber during the analyte assay, because diffusion time is long relative to the measurement time, which may be about 5 seconds or less.

Electrodes

As provided above, the sensor includes a working electrode and at least one counter electrode. The counter electrode may be a counter/reference electrode. If multiple counter electrodes are present, one of the counter electrodes will be a counter electrode and one or more may be reference electrodes. Referring to FIGS. 2A and 2B and FIGS. 3A, 3B and 4, two examples of suitable electrode configurations are illustrated.

Working Electrode

At least one working electrode is positioned on one of first substrate 12 and second substrate 14. In all of FIGS. 2A though 4, working electrode 22 is illustrated on substrate 12. Working electrode 22 extends from the sample chamber 20 to the other end of the sensor 10 as an electrode extension called a "trace". The trace provides a contact pad 23 for providing electrical connection to a meter or other device to allow for data and measurement collection, as will be described later. Contact pad 23 can be positioned on a tab 26 that extends from the substrate on which working electrode 22 is positioned, such as substrate 12. In one embodiment, a tab has more than one contact pad positioned thereon. In a second embodiment, a single contact pad is used to provide a connection to one or more electrodes; that is, multiple electrodes are coupled together and are connected via one contact pad.

Working electrode 22 can be a layer of conductive material such as gold, carbon, platinum, ruthenium dioxide, palladium, or other non-corroding, conducting material. Working electrode 22 can be a combination of two or more conductive materials. An example of a suitable conductive epoxy is ECCOCOAT CT5079-3 Carbon-Filled Conductive Epoxy Coating (available from W.R. Grace Company, Woburn, Mass.). The material of working electrode 22 typically has relatively low electrical resistance and is typically electrochemically inert over the potential range of the sensor during operation.

Working electrode 22 may be applied on substrate 12 by any of various methods, including by being deposited, such as by vapor deposition or vacuum deposition or otherwise sputtered, printed on a flat surface or in an embossed or otherwise recessed surface, transferred from a separate carrier or liner, etched, or molded. Suitable methods of printing include screen-printing, piezoelectric printing, ink jet printing, laser printing, photolithography, and painting.

As provided above, at least a portion of working electrode 22 is provided in sample chamber 20 for the analysis of analyte, in conjunction with the counter electrode.

Counter Electrode

Figure 3B:
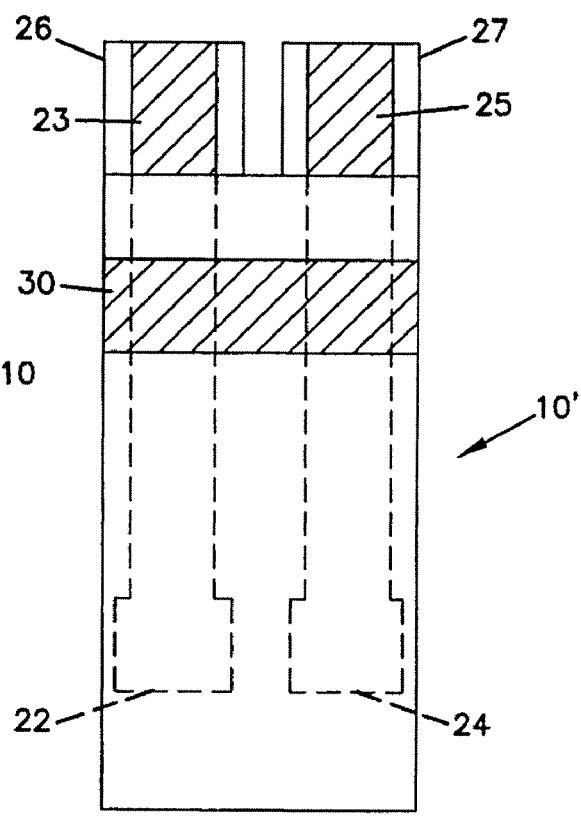
FIG. 3B is a top view of the sensor strip shown in FIG. 3A.

The sensor includes at least one counter electrode positioned within the sample chamber. In FIGS. 2A and 2B, counter electrode 24 is illustrated on substrate 14. In FIGS. 3A, 3B and 4, a counter electrode 24 is present on substrate 12. Counter electrode 24 extends from the sample chamber 20 to the other end of the sensor 10 as an electrode extension called a "trace". The trace provides a contact pad 25 for providing electrical connection to a meter or other device to allow for data and measurement collection, as will be described later. Contact pad 25 can be positioned on a tab 27 that extends from the substrate on which counter electrode 24 is positioned, such as substrate 12 or 14. In one embodiment, a tab has more than one contact pad positioned thereon. In a second embodiment, a single contact pad is used to provide a connection to one or more electrodes; that is, multiple electrodes are coupled together and are connected via one contact pad.

Counter electrode 24 may be constructed in a manner similar to working electrode 22. Suitable materials for the counter/reference or reference electrode include Ag/AgCl or Ag/AgBr on a non-conducting base material or silver chloride on a silver metal base. The same materials and methods may be used for counter electrode 24 as are available for working electrode 22, although different materials and methods may also be used. Counter electrode 24 can include a mix of multiple conducting materials, such as Ag/AgCl and carbon.

Electrode Configurations

Working electrode 22 and counter electrode 24 may be disposed opposite to and facing each other to form facing electrodes. See for example, FIG. 2A, which has working electrode 22 on substrate 12 and counter electrode 24 on substrate 14, forming facing electrodes. In this configuration, the sample chamber is typically present between the two electrodes 22, 24. For this facing electrode configuration, electrodes 22, 24 may be separated by a distance of no more than about 0.2 mm (e.g., at least one portion of the working electrode is separated from one portion of the counter electrode by no more than about 200 µm), e.g., no more than about 100 µm, e.g., no more than about 50 µm.

Working electrode 22 and counter electrode 24 can alternately be disposed generally planar to one another, such as on the same substrate, to form co-planar or planar electrodes. Referring to FIGS. 3A and 4, both working electrode 22 and counter electrode 24 occupy a portion of the surface of substrate 12, thus forming co-planar electrodes.

Sensing Chemistry

In addition to working electrode 22, sensing chemistry material(s) are preferably provided in sample chamber 20 for the analysis of the analyte. Sensing chemistry material facilitates the transfer of electrons between working electrode 22 and the analyte in the sample. Any sensing chemistry may be used in sensor strip 10, 10'; the sensing chemistry may include one or more materials.

The sensing chemistry can be diffusible or leachable, or non-diffusible or non-leachable. For purposes of discussion herein, the term "diffusible" will be used to represent "diffusible or leachable" and the term "non-diffusible" will be used to represent "non-diffusible or non-leachable" and variations thereof. Placement of sensing chemistry components may depend on whether they are diffusible or not. For example, both non-diffusible and/or diffusible component(s) may form a sensing layer on working electrode 22. Alternatively, one or more diffusible components may be present on any surface in sample chamber 20 prior to the introduction of the sample to be analyzed. As another example, one or more diffusible component(s) may be placed in the sample prior to introduction of the sample into sample chamber 20.

Electron Transfer Agent

The sensing chemistry generally includes an electron transfer agent that facilitates the transfer of electrons to or from the analyte. The electron transfer agent may be diffusible or non-diffusible, and may be present on working electrode 22 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes can be used for other analytes.

The electron transfer agent, whether it is diffusible or not, facilitates a current between working electrode 22 and the analyte and enables the electrochemical analysis of molecules. The agent facilitates the transfer electrons between the electrode and the analyte.

Redox Mediator

This sensing chemistry may, additionally to or alternatively to the electron transfer agent, include a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator can be a polymeric redox mediator, or, a redox polymer (i.e., a polymer having one or more redox species). Examples of suitable redox mediators and redox polymer are disclosed in U.S. Pat. No. 6,338,790, for example, and in U.S. Pat. Nos. 6,605,200 and 6,605,201.

If the redox mediator is non-diffusible, then the redox mediator may be disposed on working electrode 22 as a layer. In an embodiment having a redox mediator and an electron transfer agent, if the redox mediator and electron transfer agent are both non-leachable, then both components are disposed on working electrode 22 as individual layers, or combined and applied as a single layer.

The redox mediator, whether it is diffusible or not, mediates a current between working electrode 22 and the analyte and enables the electrochemical analysis of molecules which may not be suited for direct electrochemical reaction on an electrode. The mediator functions as an agent to transfer electrons between the electrode and the analyte.

Sorbent Material

Sample chamber 20 can be empty before the sample is placed in the chamber, or, in some embodiments, the sample chamber can include a sorbent material to sorb and hold a fluid sample during the measurement process. The sorbent material facilitates the uptake of small volume samples by a wicking action which can complement or, e.g., replace any capillary action of the sample chamber. Suitable sorbent materials include polyester, nylon, cellulose, and cellulose derivatives such as nitrocellulose. In addition to or alternatively, a portion or the entirety of the wall of the sample chamber may be coated by a surfactant, which is intended to lower the surface tension of the fluid sample and improve fluid flow within the sample chamber.

Methods other than the wicking action of a sorbent can be used to transport the sample into the sample chamber or measurement zone. Examples of such methods for transport include the application of pressure on a sample to push it into the sample chamber, the creation of a vacuum by a pump or other vacuum-producing method in the sample chamber to pull the sample into the chamber, capillary action due to interfacial tension of the sample with the walls of a thin sample chamber, as well as the wicking action of a sorbent material.

Fill Indicator Electrode

In some instances, it is desirable to be able to determine when the sample chamber is filled. Sensor strip 10, 10' can be indicated as filled, or substantially filled, by observing a signal between an indicator electrode and one or both of working electrode 22 or counter electrode 24 as sample chamber 20 fills with fluid. When fluid reaches the indicator electrode, the signal from that electrode will change. Suitable signals for observing include, for example, voltage, current, resistance, impedance, or capacitance between the indicator electrode and, for example, working electrode 22. Alternatively, the sensor can be observed after filling to determine if a value of the signal (e.g., voltage, current, resistance, impedance, or capacitance) has been reached indicating that the sample chamber is filled.

Typically, the indicator electrode is further downstream from a sample inlet, such as inlet 21, than working electrode 22 and counter electrode 24.

For side-fill sensors, an indicator electrode can be present on each side of the counter electrode. This permits the user to fill the sample chamber from either the left or right side with an indicator electrode disposed further upstream. This three-electrode configuration is not necessary. Side-fill sensors can also have a single indicator electrode and may include some indication as to which side should be placed in contact with the sample fluid.

The indicator electrode can also be used to improve the precision of the analyte measurements. The indicator electrode may operate as a working electrode or as a counter electrode or counter/reference electrode. Measurements from the indicator electrode/working electrode can be combined (for example, added or averaged) with those from the first counter/reference electrode/working electrode to obtain more accurate measurements.

The sensor or equipment that the sensor connected is with (e.g., a meter) can include a sign (e.g., a visual sign or auditory signal) that is activated in response to the indicator electrode to alert the user that the measurement zone has been filled. The sensor or equipment can be configured to initiate a reading when the indicator electrode indicates that the measurement zone has been filled with or without alerting the user. The reading can be initiated, for example, by applying a potential between the working electrode and the counter electrode and beginning to monitor the signals generated at the working electrode.

Insertion Monitor

In accordance with this invention, the sensor includes an indicator to notify when proper insertion of sensor strip 10, 10' into receiving equipment, such as a meter, has occurred. As seen in FIGS. 1, 2A, 2B, 3A and 3B, sensor strips 10, 10' include insertion monitor 30 on an exterior surface of one of substrates 12, 14.

Insertion monitor 30 is used to encode information regarding sensor strip 10, 10'. The encoded information can be, for example, calibration information for that manufacturing lot or for that specific strip. Such calibration information or code may relate to, e.g., the sensitivity of the strip or to the y-intercept and/or slope of its calibration curve. The calibration code is used by the meter or other equipment to which sensor strip 10, 10' is connected to provide an accurate analyte reading. For example, based on the calibration code, the meter uses one of several programs stored within the meter.

In some embodiments, a value indicative of the calibration code is manually entered into the meter or other equipment, for example, by the user. In other embodiments, the calibration code is directly read by the meter or other equipment, thus not requiring input or other interaction by the user.

Figure 5A:
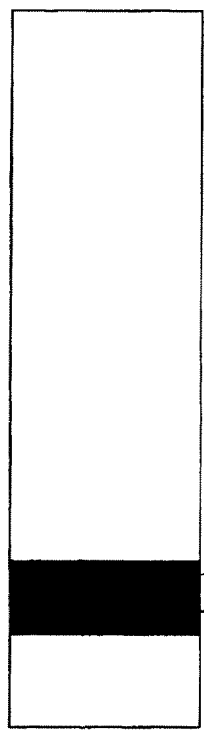
FIG. 5A is a top view of a first example configuration for a suitable insertion monitor in accordance with the present invention.

In one embodiment, illustrated, for example in FIG. 5A, insertion monitor 30 is a stripe 130 extending across an exterior surface of sensor 10, 10', for example, from side edge to side edge, with one contact pad for connection to a meter. It is understood that in alternate embodiments stripe 130 need not extend to both side edges. In another embodiment, the insertion monitor comprises two or more contact pads for connection to a meter. The two or more contact pads are electrically connected to each other by a material, such as a conductive ink.

The calibration code can be designed into insertion monitor 30, for example, either by the resistance or other electrical characteristic of insertion monitor 30, by the placement or position of insertion monitor 30, or by the shape or configuration of insertion monitor 30.

Insertion monitor 30 may alternately or additionally carry other information regarding the sensor strip 10, 10'. This other information that could be encoded into insertion monitor 30 include the test time needed for accurate analyte concentration analysis, expiration date of the sensor strip 10, 10', various correction factors, such as for environmental temperature and/or pressure, selection of the analyte to be analyzed (e.g., glucose, ketone, lactate), and the like.

The resistance of insertion monitor 30, such as that of single stripe 130 or area or of a conductive path between the two or more contact pads, is related to the encoded information. As an example of discrete calibration values, resistance values in a given range can correspond to one calibration setting, and resistance values in a different range can correspond to a different calibration setting. Thus, when a meter or other equipment receives a sensor strip, indicator monitor 30 will notify the meter or equipment which assay calculation to use.

In addition to varying the resistance of indicator monitor 30 by varying the conductive or semi-conductive material used, the resistance of indicator monitor 30 can be varied by cutting or scoring some or all of the conductive pathways so that they do not carry charge. The resistance can additionally or alternately be controlled by the width or length of the conductive path. An example of a material suitable for indicator monitor 30 is a combination of carbon and silver; the resistance of this mixture will vary, based on the ratio of the two materials.

The placement or position of insertion monitor 30 can additionally or alternately be related to the encoded calibration information. For example, the calibration code can be directly related to the location of indicator monitor 30. For example, the position of indicator monitor 30 can be varied so that is makes electrical contact with different contact structures. (Contact structures are described below in "Sensor Connection to Electrical Device"). Depending on the contact structures engaged, the meter will recognize the calibration code and thus know what parameter to use to calculate an accurate analyte level.

The shape and/or configuration of insertion monitor 30 can additionally or alternatively be related to the encoded calibration code. For example, the calibration code can be directed related to which and/or the number of contact structures that make electrical contact with indicator monitor 30. For example, a pattern of discrete and unconnected indicator monitors can be present on the sensor; the calibration code will be directly related to the arrangement of those monitors. The pattern could be parallel lines, orderly arranged dots or squares, or the like.

While it is preferred to provide this encoded information on the insertion monitor, it should be recognized that the insertion monitor function and the encoding of information can also be implemented separately using separate conductive traces on the strip.

Conductive insertion monitor 30 is positioned on the non-conductive base substrate and has a contact pad for electrical contact with a connector. Insertion monitor 30 is configured and arranged to close an electrical circuit when sensor 10, 10' is properly inserted into the connector.

Figure 5B:
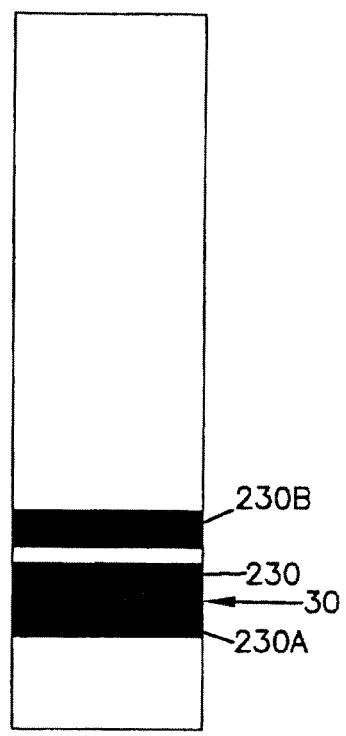
FIG. 5B is a top view of a second example configuration for a suitable insertion monitor in accordance with the present invention.
Figure 5C:
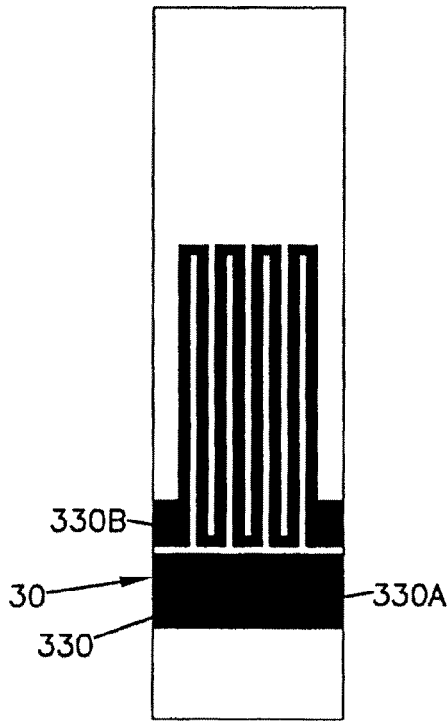
FIG. 5C is a top view of a third example configuration for a suitable insertion monitor in accordance with the present invention.
Figure 5D:
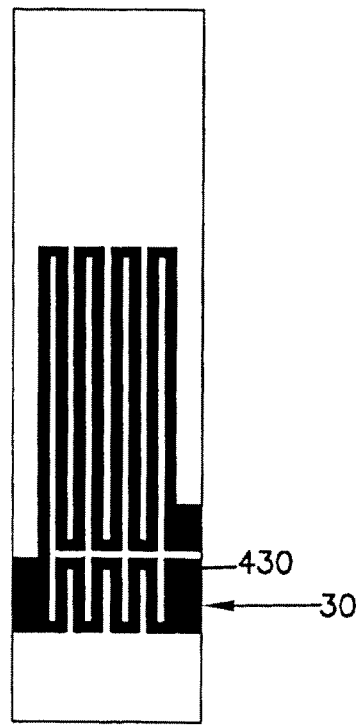
FIG. 5D is a top view of a fourth example configuration for a suitable insertion monitor in accordance with the present invention.

Insertion monitor 30 may have any suitable configuration, including but not limited to, a stripe extending across sensor strip 10, 10' from a side edge to a side edge, such as stripe 130, a stripe extending across the sensor strip, although not the entire width, and an array of unconnected dots, strips, or other areas. Other suitable configurations for insertion monitor 30 are illustrated in FIGS. 5B, 5C and 5D. FIG. 5B illustrates insertion monitor 30 as bi-regional monitor 230, having a first stripe 230A and a second stripe 230B, both of which extend from side edge to side edge, although it is understood that one or both of strips 230A, 230B may not extend completely to a side edge. FIGS. 5C and 5D illustrate insertion monitors that have a long, tortuous path, which extends longitudinally toward an end of the sensor, rather than extending merely side-to-side. Insertion monitor 330 of FIG. 5C has a stripe 330A and an elongate stripe 330B. Insertion monitor 430 of FIG. 5D has a single conductive strip 430, which provides an elongate path.

Sensor Connection to Electrical Device

Referring to FIGS. 7A, 7B, 8A, 8B, 9A and 9B, a sensor strip 100 is illustrated readied for insertion into a connector 500. Sensor strip 100 is similar to sensor strips 10, 10'. Sensor strip 100 includes insertion monitor 30 on an outer surface of one of the substrates forming strip 100. Sensor strip 100 includes, although not illustrated, one working electrode and three counter electrodes. The working electrode includes a contact pad positioned on tab 123 (see FIGS. 7A and 9A). Each of the three counter electrodes includes a contact pad positioned on tab 124, 125, 126, respectively (see FIG. 9A).

Sensor strip 100 is configured to couple to a meter or other electrical device by electrical connector 500 which is configured to couple with and contact the end of sensor 100 at contact pads 123, 124, 125, 126. The sensor meter typically includes a potentiostat or other component to provide a potential and/or current for the electrodes of the sensor. The sensor reader also typically includes a processor (e.g., a microprocessor or hardware) for determining analyte concentration from the sensor signals. The sensor meter also includes a display or a port for coupling a display to the sensor. The display displays the sensor signals and/or results determined from the sensor signals including, for example, analyte concentration, rate of change of analyte concentration, and/or the exceeding of a threshold analyte concentration (indicating, for example, hypo- or hyperglycemia).

One example of a suitable connector is shown in FIGS. 7A and 7B, 8A and 8B, and 9A and 9B. Connector 500 (which is used to connect a sensor to a meter or other electrical device) is generally a two part structure, having top portion 510 and bottom portion 520 (see FIG. 7B). Positioned between and secured by top portion 510 and bottom portion 520 are various contact leads that provide electrical connection between sensor 100 and a meter. Bottom portion includes leads 51, 52 and 223, 224, 225, 226, as will be described below.

Leads 223, 224, 225, 226, have proximal ends to physically contact pads 123, 124, 125, 126, respectively, and to connect to any attached meter. Each pad 123, 124, 125, 126 has its respective lead 223, 224, 225, 226. The end of sensor 100 having the contact pads can be slid into or mated with connector 500 by placing sensor 100 into slide area 530, which provides a support for and retains sensor 100. It is typically important that the contact structures of the connector 500 make electrical contact with the correct pads of the sensor so that the working electrode and counter electrode(s) are correctly coupled to the meter.

Connector 500 includes leads or contact structures 51, 52 for connection to insertion monitor 30. Insertion monitor 30 is configured and arranged to close an electrical circuit between contact structures 51 and 52 when the sensor is properly inserted into the connector. Proper insertion into connector 500 means that the sensor strip 100 is inserted right side up, that the correct end of strip 100 is inserted into connector 500, and that sensor strip 100 is inserted far enough into connector 500 that reliable electrical connections are made between the electrode contact pads 123, 124, 125, 126 and the corresponding contacts leads 223, 224, 225, 226. Preferably, no closed circuit is made unless all electrode pads have properly contacted the contact structures of connector 500. The insertion monitor may have shapes other than a stripe across the width of the sensor; for example, other designs include an individual dot, a grid pattern, or may include stylistic features, such as words or letters.

Because this insertion monitor 30 is not at the end with the contact regions for the electrodes, the insertion monitor 30 does not require additional width space on the sensor. The width of the contact pads 123, 124, 125, 126 is defined as the width on which a lead could be placed that would result in an electrical connection; typically, the contact width is the width of the exposed contact area. In one embodiment, six contact lead structures on the connector (e.g., 52, 223, 224, 225, 226, 51) can contact sensor 100 in the same width as the four contact pads (e.g., 123, 124, 125, 126). This concept of having contact points on the sensor that occupy more width than the width of the sensor may be used for any number of contact points; this may be used with or without an insertion monitor 30.

As a particular example, four leads 223, 224, 225, 226 make contact with contact pads 123, 124, 125, 126. If each lead and/or contact pad is one millimeter wide, a sensor of at least 4 mm wide is needed to make contact. Additional leads, such as those for insertion monitor 30 (i.e., contact leads 51, 52), can make contact by having leads 51, 52 extend along the side of leads 223, 226 and then angle in toward the center of strip 100 after the point where leads 223, 224, 225, 226 contact strip 100. The insertion monitor leads 51, 52 cross side edges of sensor 100 to make contact with the sensor, thus not requiring additional sensor width.

The contact structures are generally parallel and non-overlapping. The lead structures 223, 224, 225, 226 terminate in close proximity to the proximal end of sensor strip 100 (e.g., on contact pads 123, 124, 125, 126), but lead structures 51, 52 continue longitudinally past the proximal end of lead structures 223, 224, 225, 226 further toward the distal end of sensor strip 100. Once past the proximal end and past lead structures 223, 224, 225, 226, lead structures 51, 52 angle in toward the center of the sensor strip.

In an optional embodiment to ensure proper insertion of a sensor into a meter, the meter may include a raised area or bump that prevents or hinders the insertion of the sensor in an improper direction. Objects other than a raised area can also be used to guide the user in correct introduction of the sensor into the meter.

General Method for Manufacturing Sensors

Figure 6A:
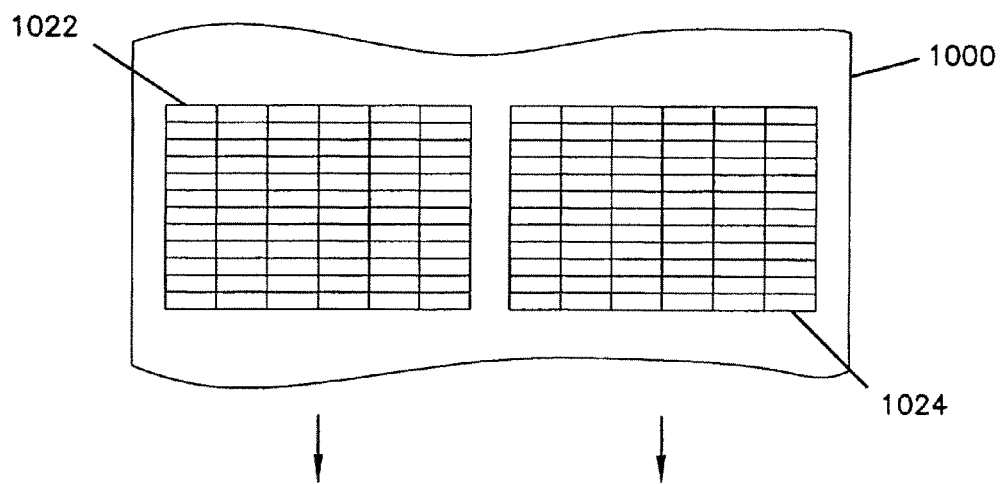
FIG. 6A illustrates a top view of one embodiment of a sheet of sensor components, according to the invention.
Figure 6B:
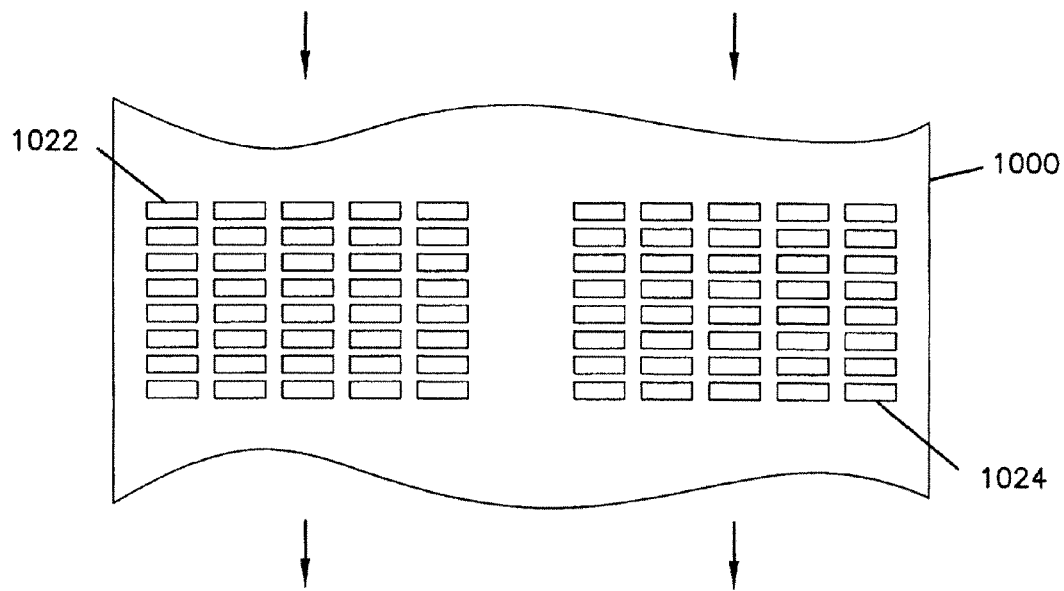
FIG. 6B illustrates a top view of another embodiment of a sheet of sensor components, according to the invention.
Figure 7B:
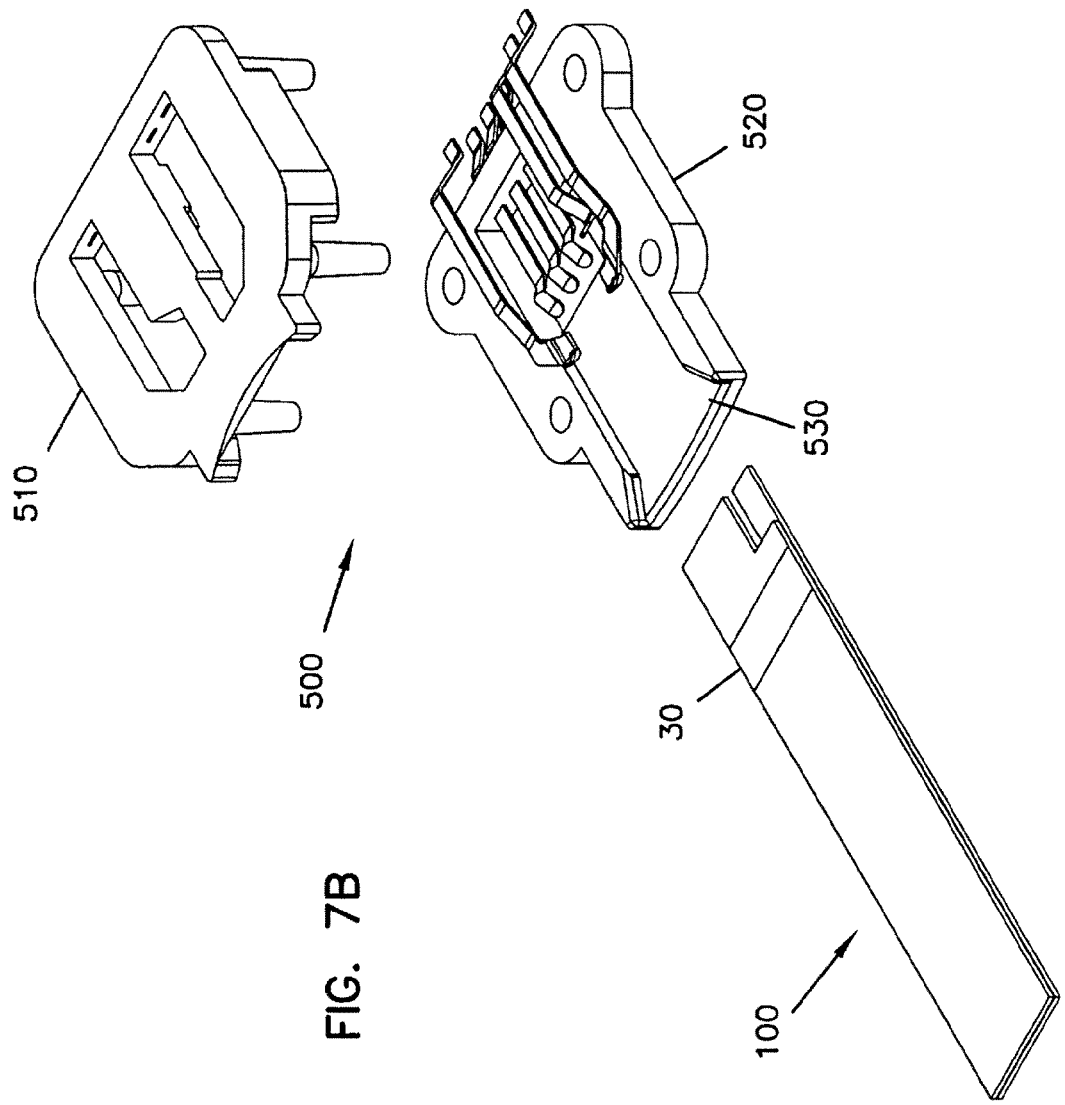
FIG. 7B is an exploded view of the electrical connector device of FIG. 7A.
Figure 8B:
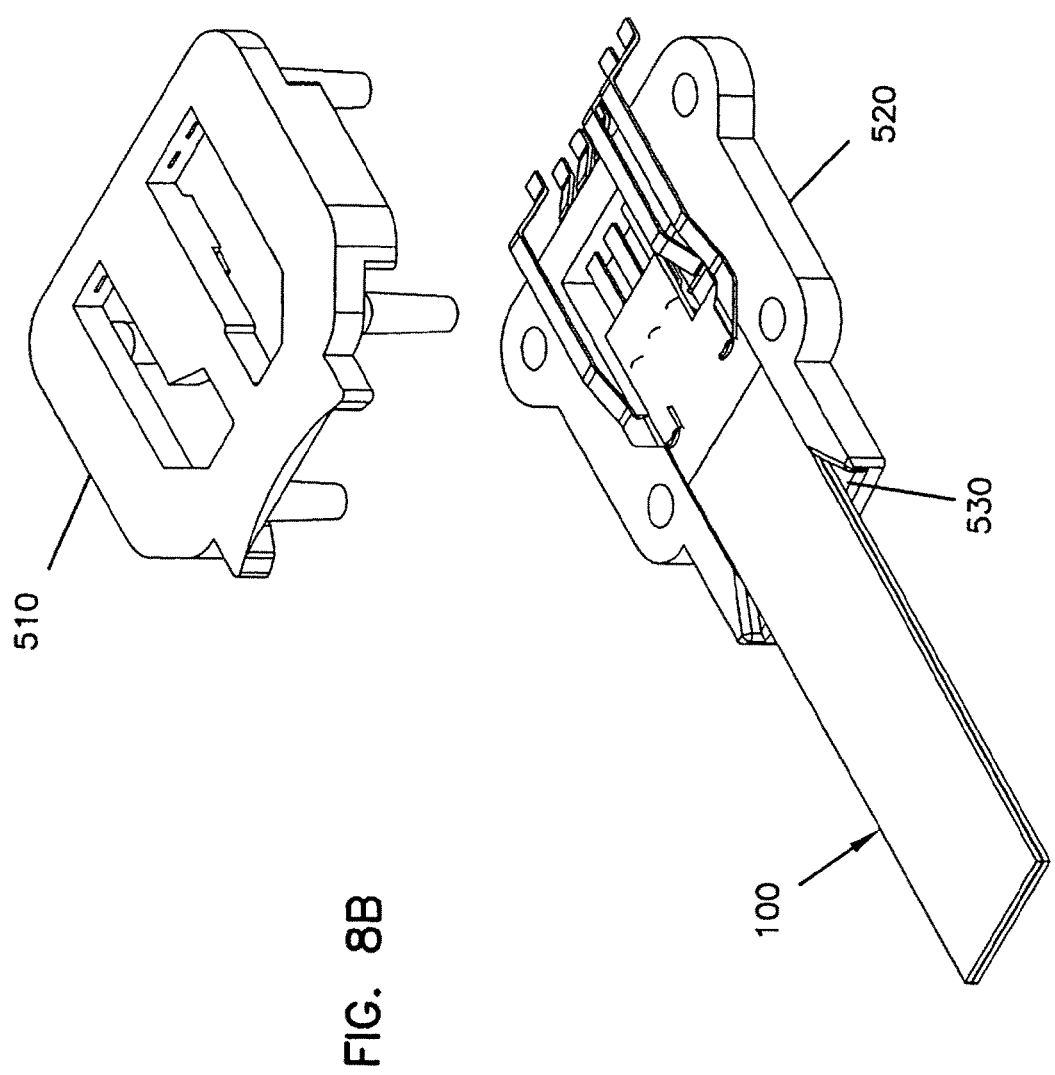
FIG. 8B is an exploded view of the electrical connector device of FIG. 8A.
Figure 9A:
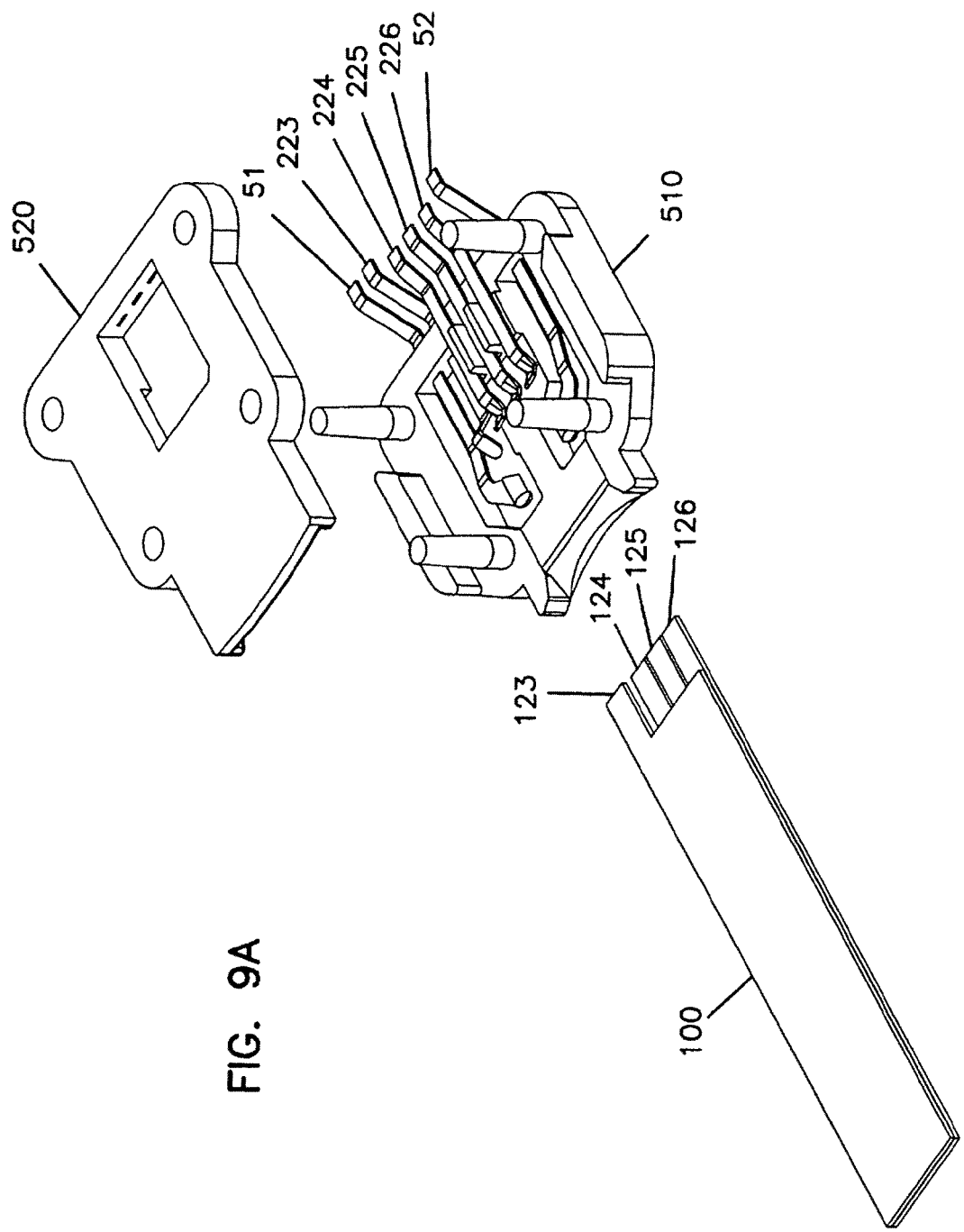
FIG. 9A is a bottom perspective view of the electrical connector device of FIGS. 7A and 7B.
Figure 9B:
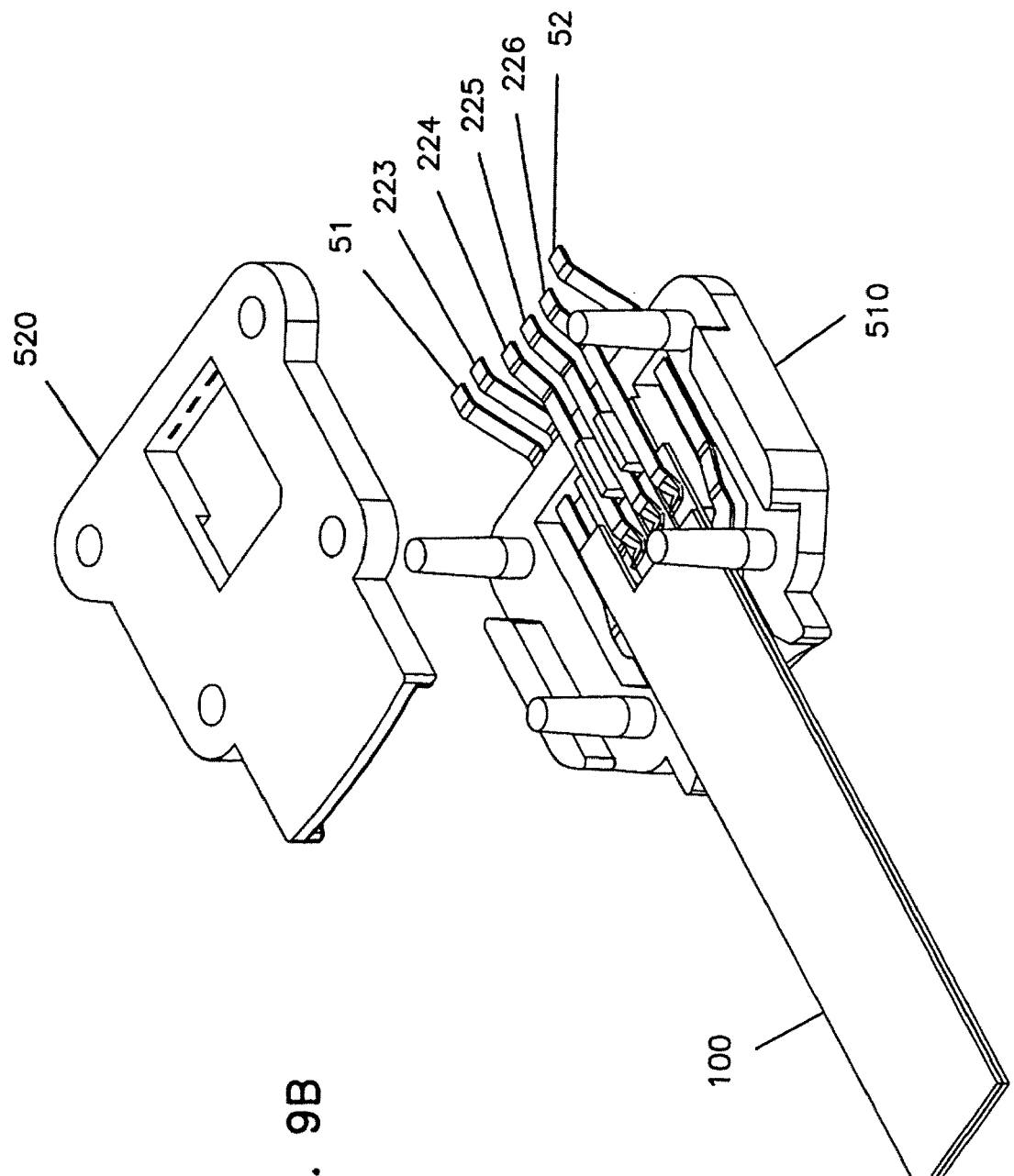
FIG. 9B is a bottom perspective view of the electrical connector device of FIGS. 8A and 8B.

Referring now to FIGS. 6A and 6B, one example of a method for making sensors having two substrates with electrodes thereon is described with respect to the sensor arrangement displayed in FIG. 2A, although this method can be used to make a variety of other sensor arrangements, including those described before. When the three layers of FIG. 2A are assembled, a sensor similar to sensor 10 is formed.

In FIGS. 6A and 6B, a substrate 1000, such as a plastic substrate, is moving in the direction indicated by the arrow. Substrate 1000 can be an individual sheet or a continuous roll on a web. Multiple sensors can be formed on substrate 1000 as sections 1022 that have working electrodes 22 (FIG. 2A) thereon and sections 1024 that have counter electrodes 24 (FIG. 2A) thereon and other electrodes, such as reference electrodes and/or fill indicator electrodes. These working, counter and optional electrodes are electrically connected to their corresponding traces and contact pads. Typically, working electrode sections 1022 are produced on one half of substrate 1000 and counter electrode sections 1024 are produce on the other half of substrate 1000. In some embodiments, substrate 1000 can be scored and folded to bring the sections 1022, 1024 together to form the sensor. In some embodiments, as illustrated in FIG. 6A, the individual working electrode sections 1022 can be formed next to or adjacent each other on substrate 1000, to reduce waste material. Similarly, individual counter electrode sections 1024 can be formed next to or adjacent each other. In other embodiments, the individual working electrode sections 1022 (and, similarly, the counter electrode sections 1024) can be spaced apart, as illustrated in FIG. 6B. The remainder of the process is described for the manufacture of multiple sensors, but can be readily modified to form individual sensors.

Carbon or other electrode material (e.g., metal, such as gold or platinum) is formed on substrate 1000 to provide a working electrode 22 for each sensor. The carbon or other electrode material can be deposited by a variety of methods including printing a carbon or metal ink, vapor deposition, and other methods. The printing may be done by screen printing, gravure roll printing, transfer printing, and other known printing methods. The respective trace and contact pad 23 could be applied together with working electrode 22, but may be applied in a subsequent step.

Similar to the working electrode 22, counter electrode 24 is formed on substrate 1000. The counter electrode(s) are formed by providing carbon or other conductive electrode material onto substrate 1000. In one embodiment, the material used for the counter electrode(s) is a Ag/AgCl ink. The material of the counter electrode(s) may be deposited by a variety of methods including printing or vapor deposition. The printing may be done by screen printing, gravure roll printing, transfer printing, and other known printing methods. The respective trace and contact pad 25 could be applied together with counter electrodes 24, but may be applied in a subsequent step.

Preferably, multiple sensors 10 are manufactured simultaneously; that is, the working electrodes, including their traces and contact pads, for a plurality of sensors are produced (e.g., printed) on a polymer sheet or web, and simultaneously or subsequently, the counter electrodes, and their traces and contact pads, for a plurality of sensors are produced (e.g., printed). The working electrode(s) and counter electrode(s) can be formed on separate substrates that are later positioned opposite one another so that the electrodes face each other. Alternately, to simplify registration of the substrates, the working electrodes can be formed on a first half of a substrate sheet of web and the counter electrodes are formed on a second half of the substrate sheet or web so that the sheet or web can be folded to superimpose the working and counter electrodes in a facing arrangement.

To provide sample chamber 20, spacer 15 is formed over at least one of the substrate/working electrode and substrate/ counter electrode(s). Spacer 15 can be an adhesive spacer, such as a single layer of adhesive or a double-sided adhesive tape (e.g., a polymer carrier film with adhesive disposed on opposing surfaces). Suitable spacer materials include adhesives such as urethanes, acrylates, acrylics, latexes, rubbers and the like.

A channel, which will result in the sample chamber, is provided in spacer 15, either by cutting out a portion of the adhesive spacer or placing two adhesive pieces in close proximity but having a gap therebetween. The adhesive can be printed or otherwise disposed on the substrate according to a pattern which defines the channel region. The adhesive spacer can be optionally provided with one or more release liners prior to its incorporation into the sensor. The adhesive can be cut (e.g., die-cut or slit) to remove the portion of the adhesive corresponding to the channel prior to disposing the spacer on the substrate.

Any sensing chemistry is disposed onto the substrate in at least the sample chamber regions. If any of the sensing chemistry component(s) is non-leachable, that component is preferably disposed on the working electrode. If any of the sensing chemistry component(s) is diffusible, that component can be disposed on any surface of the substrate in the channel region. The redox mediator and/or electrode transfer agent can be disposed independently or together on the substrate prior to or after placement of the spacer. The redox mediator and/or electrode transfer agent may be applied by a variety of methods including, for example, screen printing, ink jet printing, spraying, painting, striping along a row or column of aligned and/or adjacent electrodes, and the like. Other components can be deposited separately or together with the redox mediator and/or electrode transfer agent; these components can include, for example, surfactants, polymers, polymer films, preservatives, binders, buffers, and cross-linkers.

After disposing the spacer, redox mediator, second electron transfer agent, sensing layers, and the like, the first and second substrates (having the working and counter electrodes thereon) are positioned opposite each other to form the sensor. The faces of the substrate are joined by the adhesive of the spacer. After bringing the faces together, individual sensors can be cut out from the web of sensors using a variety of methods including, for example, die cutting, slitting, or otherwise cutting away the excess substrate material and separating the individual sensors. In some embodiments, a combination of cutting or slitting methods is used. As another alternative, the individual sensor components can first be cut out of the substrates and then brought together to form the sensor by adhesively joining the two components, such as by using the spacer adhesive.

The sides of the sensor can be straight to allow the sensor to be cut out from the remainder of the substrate and/or from other sensors by slitting the substrate in parallel directions using, for example, a gang arbor blade system. The edges of the sensor can define edges of the sample chamber and/or measurement zone. By accurately controlling the distance between cuts, variability in sample chamber volume can often be reduced. In some instances, these cuts are parallel to each other, as parallel cuts are typically the easiest to reproduce.

Application of the Sensor

A common use for the analyte sensor of the present invention, such as sensor strip 10, 10', 100 is for the determination of analyte concentration in a biological fluid, such as glucose concentration in blood, interstitial fluid, and the like, in a patient or other user. Sensor strips 10, 10', 100 may be available at pharmacies, hospitals, clinics, from doctors, and other sources of medical devices. Multiple sensor strips 10, 10', 100 may be packaged together and sold as a single unit; e.g., a package of 25, 50, or 100 strips.

Sensor strips 10, 10', 100 can be used for an electrochemical assay, or, for a photometric test. Sensor strips 10, 10', 100 are generally configured for use with an electrical meter, which may be connectable to various electronics. A meter may be available at generally the same locations as sensor strips 10, 10', 100 and sometimes may be packaged together with sensor strips 10, 10', 100, e.g., as a kit.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device does have a display, such as a liquid crystal display (LCD), as well as an input device, such as buttons, a keyboard, mouse or touch-screen. With such an arrangement, the user can control the meter indirectly by interacting with the user interface(s) of the server device, which in turn interacts with the meter across a wireless link.

The server device can also communicate with another device, such as for sending glucose data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as sensor strips 10 and the meter, and sometimes may be packaged together with sensor strips 10 and/or meter, e.g., as a kit.

Integrated Sample Acquisition and Analyte Measurement Device

An analyte measurement device constructed according to the principles of the present invention typically includes a sensor strip 10, 10', 100, as described hereinabove, combined with a sample acquisition apparatus to provide an integrated sampling and measurement device. The sample acquisition apparatus typically includes, for example, a skin piercing member, such as a lancet, that can be injected into a patient's skin to cause blood flow. The integrated sample acquisition and analyte measurement device can comprise a lancing instrument that holds a lancet and sensor strip 10, 10', 100. The lancing instrument might require active cocking. By requiring the user to cock the device prior to use, the risk of inadvertently triggering the lancet is minimized. The lancing instrument could also permit the user to adjust the depth of penetration of the lancet into the skin. Such devices are commercially available from companies such as Boehringer Mannheim and Palco. This feature allows users to adjust the lancing device for differences in skin thickness, skin durability, and pain sensitivity across different sites on the body and across different users.

In one embodiment, the lancing instrument and the meter are integrated into a single device. To operate the device the user need only insert a disposable cartridge containing a sensor strip and lancing device into the integrated device, cock the lancing instrument, press it against the skin to activate it, and read the result of the measurement. Such an integrated lancing instrument and test reader simplifies the testing procedure for the user and minimizes the handling of body fluids.

In some embodiments, sensor strips 10, 10' may be integrated with both a meter and a lancing device. Having multiple elements together in one device reduces the number of devices needed to obtain an analyte level and facilitates the sampling process.

For example, embodiments may include a housing that includes one or more of the subject strips, a skin piercing element and a processor for determining the concentration of an analyte in a sample applied to the strip. A plurality of strips 10, 10', 100 may be retained in a cassette in the housing interior and, upon actuation by a user, a single strip 10, 10' may be dispensed from the cassette so that at least a portion extends out of the housing for use.

Operation of the Sensor Strip

In use, a sample of biological fluid is provided into the sample chamber of the sensor, where the level of analyte is determined. The analysis may be based on providing an electrochemical assay or a photometric assay. In many embodiments, it is the level of glucose in blood that is determined. Also in many embodiments, the source of the biological fluid is a drop of blood drawn from a patient, e.g., after piercing the patient's skin with a lancing device, which could be present in an integrated device, together with the sensor strip.

The analyte in the sample is, e.g., electrooxidized or electroreduced, at working electrode 22, and the level of current obtained at counter electrode 24 is correlated as analyte concentration.

Sensor strip 10, 10', 100 may be operated with or without applying a potential to electrodes 22, 24. In one embodiment, the electrochemical reaction occurs spontaneously and a potential need not be applied between working electrode 22 and counter electrode 24. In another embodiment, a potential is applied between working electrode 22 and counter electrode 24.

The invention has been described with reference to various specific and preferred embodiments and techniques. However, it will be apparent to one of ordinarily skill in the art that many variations and modifications may be made while remaining within the spirit and scope of the invention.

All patents and other references in this specification are indicative of the level of ordinary skill in the art to which this invention pertains. All patents are herein incorporated by reference to the same extent as if each individual patent was specifically and individually incorporated by reference.

We claim:

1. A meter for releasable engagement with a sensor, the meter comprising an electrical connector for receiving a sensor, the electrical connector comprising:
   a support for receiving the sensor;
   a first contact structure and a second contact structure configured to contact an insertion monitor present on a surface of the sensor, wherein the meter contacts the insertion monitor at only two contact points to recognize a resistance value corresponding to a calibration code for the sensor from the insertion monitor; and
   a third contact structure configured to contact a working electrode and a fourth contact structure configured to contact a counter electrode, wherein the working electrode is disposed on a surface of the sensor and a counter electrode is disposed on a surface of the sensor,
   wherein each of the contact structures have a proximal end for contacting the sensor and a distal end for connection to the meter,
   wherein the third and fourth contact structures extend longitudinally from the distal to the proximal end and wherein the third and fourth contact structures are parallel to each other,
   wherein the first and second contact structures extend longitudinally next to the third and fourth contact structures, past the proximal ends of the third and fourth contact structures,
   wherein the first and second contact structures are longer than the third and fourth contact structures, and
   wherein the first contact structure is oriented to extend across a first side edge of the sensor and the second contact structure is oriented to extend across a second side edge of the sensor, wherein the first and second contact structures angle towards a longitudinal center line of the sensor.

2. The meter of claim 1 configured to recognize the calibration code based on a position of the insertion monitor.

3. A system for determining the concentration of an analyte in a sample, the system comprising:
   an analyte sensor for determining the concentration of an analyte in a sample, the sensor comprising:
      a first end and a second end opposite to the first end, a first side edge extending between the first and second ends and a second side edge opposite the first side edge and extending between the first and second ends;
      an insertion monitor having a resistance value corresponding to a calibration code for the sensor, wherein the insertion monitor is present on a surface of the sensor; and
      a working electrode disposed on a surface of the sensor and a counter electrode is disposed on a surface of the sensor; and
   a meter comprising an electrical connector for receiving the sensor, the electrical connector comprising:
      a first contact structure and a second contact structure configured for electrical connection to the insertion monitor, wherein the meter contacts the insertion monitor at only two contact points to recognize the resistance value corresponding to the calibration code; and
      a third contact structure configured to contact the working electrode and a fourth contact structure configured to contact the counter electrode,
   wherein each of the contact structures have a proximal end for contacting the sensor and a distal end for connection to the meter,
   wherein the third and fourth contact structures extend longitudinally from the distal to the proximal end and wherein the third and fourth contact structures are parallel to each other,
   wherein the first and second contact structures extend longitudinally next to the third and fourth contact structures, past the proximal ends of the third and fourth contact structures,
   wherein the first and second contact structures are longer than the third and fourth contact structures,
   wherein the first contact structure is oriented to extend across the first side edge of the sensor and the second contact structure is oriented to extend across the second side edge of the sensor, and
   wherein the first and second contact structures angle towards a longitudinal center line of the sensor.

4. The system of claim 3, wherein the insertion monitor comprises carbon and/or silver.

5. The system of claim 3, wherein the calibration code is based on a pattern of conductive areas that form the insertion monitor.

6. The system of claim 3, wherein the insertion monitor is a conductive stripe.

7. The system of claim 3, wherein the insertion monitor is a conductive dot.

8. The system of claim 3, wherein the insertion monitor is a conductive grid pattern.

9. The system of claim 3, wherein the insertion monitor is a conductive stylistic feature.

10. A meter for releasable engagement with a sensor, the meter comprising an electrical connector for receiving a sensor, the electrical connector comprising:
    a support for receiving the sensor;
    a first contact structure and a second contact structure configured to contact an insertion monitor present on a surface of the sensor, wherein the meter contacts the insertion monitor at only two contact points to recognize a resistance value corresponding to a calibration code for the sensor from the insertion monitor; and
    a third contact structure configured to contact a working electrode and a fourth contact structure configured to contact a counter electrode, wherein the working electrode is disposed on a surface of the sensor and a counter electrode is disposed on a surface of the sensor,
    wherein each of the contact structures have a proximal end for contacting the sensor and a distal end for connection to the meter,
    wherein the third and fourth contact structures extend longitudinally from the distal to the proximal end and wherein the third and fourth contact structures are parallel to each other,
    wherein the first and second contact structures extend longitudinally next to the third and fourth contact structures, past the proximal ends of the third and fourth contact structures,
    wherein the first and second contact structures are longer than the third and fourth contact structures, and
    wherein the third and fourth contact structures are positioned in between the first and second contact structures and wherein the portions of the first and second contact structures that extend past the proximal ends of the third and fourth contact structures angle in opposite directions towards a longitudinal center line of the support for receiving the sensor.

11. The meter of claim 10 configured to recognize the calibration code based on a position of the insertion monitor.

* * * * *